(12) United States Patent
Pouget et al.

(10) Patent No.: US 11,464,407 B2
(45) Date of Patent: Oct. 11, 2022

(54) DETERMINATION OF CHROMATIC ISO-LUMINANCE INFORMATION FOR CONTROLLING A COMPUTER PROCESS IN A PERSONALISED MANNER

(71) Applicants: INSTITUT DU CERVEAU ET DE LA MOELLE EPINIERE (ICM), Paris (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); ASSISTANCE PUBLIQUE-HOPITAUX DE PARIS (AP-HP), Paris (FR); SORBONNE UNIVERSITE, Paris (FR)

(72) Inventors: Pierre Pouget, Paris (FR); Alexis Genin, St Leu d'Esserent (FR)

(73) Assignees: INSTITUT DU CERVEAU ET DE LA MOELLE EPINIERE (ICM), Paris (FR); CENTRE NATIONAL DE LA RECHERCHE SCIENTIFIQUE (CRNS), Paris (FR); INSTITUT NATIONAL DE LA SANTE ET DE LA RECHERCHE MEDICALE (INSERM), Paris (FR); ASSISTANCE PUBLIQUE-HOPITAUX DE PARIS (AP-HP), Paris (FR); SORBONNE UNIVERSITE, Paris (FR)

(*) Notice: Subject to any disclaimer, the term of this patent is extended or adjusted under 35 U.S.C. 154(b) by 462 days.

(21) Appl. No.: 16/499,782

(22) PCT Filed: Mar. 29, 2018

(86) PCT No.: PCT/EP2018/058120
§ 371 (c)(1),
(2) Date: Sep. 30, 2019

(87) PCT Pub. No.: WO2018/178258
PCT Pub. Date: Oct. 4, 2018

(65) Prior Publication Data
US 2020/0037870 A1 Feb. 6, 2020

(30) Foreign Application Priority Data

Mar. 31, 2017 (FR) .................................. 1752814

(51) Int. Cl.
*A61B 3/06* (2006.01)
*A61B 3/00* (2006.01)
(Continued)

(52) U.S. Cl.
CPC ............ *A61B 3/066* (2013.01); *A61B 3/0025* (2013.01); *A61B 3/0325* (2013.01); *A61B 5/117* (2013.01)

(58) Field of Classification Search
CPC ......... A61B 3/112; A61B 3/145; A61B 3/066; A61B 3/0025; A61B 3/0325
(Continued)

(56) References Cited

U.S. PATENT DOCUMENTS

| 5,141,305 A | 8/1992 | Young |
| 11,229,356 B2 * | 1/2022 | Pouget .................. A61B 3/145 |

FOREIGN PATENT DOCUMENTS

EP    1219243 A1    7/2002

OTHER PUBLICATIONS

Binda, P., Straβer, T., Stingl, K. et al. Pupil response components: attention-light interaction in patients with Parinaud's syndrome. Sci Rep 7, 10283 (2017). https://doi.org/10.1038/s41598-017-10816-x (Year: 2017).*

(Continued)

*Primary Examiner* — Zachary W Wilkes
(74) *Attorney, Agent, or Firm* — Osha Bergman Watanabe & Burton LLP

(57) ABSTRACT

A method for generating an indicator or biomarker of colour perception in a mammalian subject, where the method may include submitting the mammalian subject to a multicoloured dynamic stimulus comprising displaying, on a display device. The method may include controlling a change over time of at least one of the two colours of the multicolour pattern when displaying the dynamic multicolour stimulus, to vary the displayed luminance of this colour (usually several times). The method may include acquiring, by using (Continued)

an image acquisition device, an oscillatory response of a pupil of the mammalian subject. The method may include generating, from the acquired response, a signal representative of the power of the pupil's oscillatory response as a function of the change over time of at least one of the two colours when displaying the dynamic multicoloured stimulus.

20 Claims, 9 Drawing Sheets

(51) Int. Cl.
*A61B 3/032* (2006.01)
*A61B 5/117* (2016.01)

(58) Field of Classification Search
USPC .......................................................... 351/206
See application file for complete search history.

(56) References Cited

OTHER PUBLICATIONS

Corinne F. Carle, Andrew C. James, Ted Maddess; The Pupillary Response to Color and Luminance Variant Multifocal Stimuli. Invest. Ophthalmol. Vis. Sci. 2013;54(1):467-475. doi: https://doi.org/10.1167/iovs.12-10829 (Year: 2013).*

Wang CA, Boehnke SE, Itti L, Munoz DP. Transient pupil response is modulated by contrast-based saliency. J Neurosci. Jan. 8, 2014;34(2):408-17. doi: 10.1523/JNEUROSCI.3550-13.2014. PMID: 24403141; PMCID: PMC6608151 (Year: 2014).*

Gamlin, Paul D.R, et al. "Pupil Responses to Stimulus Color, Structure and Light Flux Increments in the Rhesus Monkey." Vision Research, vol. 38, No. 21, 1998, pp. 3353-3358., doi:10.1016/s0042-6989(98)00096-0 (Year: 1998).*

International Search Report issued in PCT/EP2018/058120 dated Jun. 15, 2018 (5 pages).

Written Opinion of the International Searching Authority issued in PCT/EP2018/058120 dated Jun. 15, 2018 (5 pages).

* cited by examiner

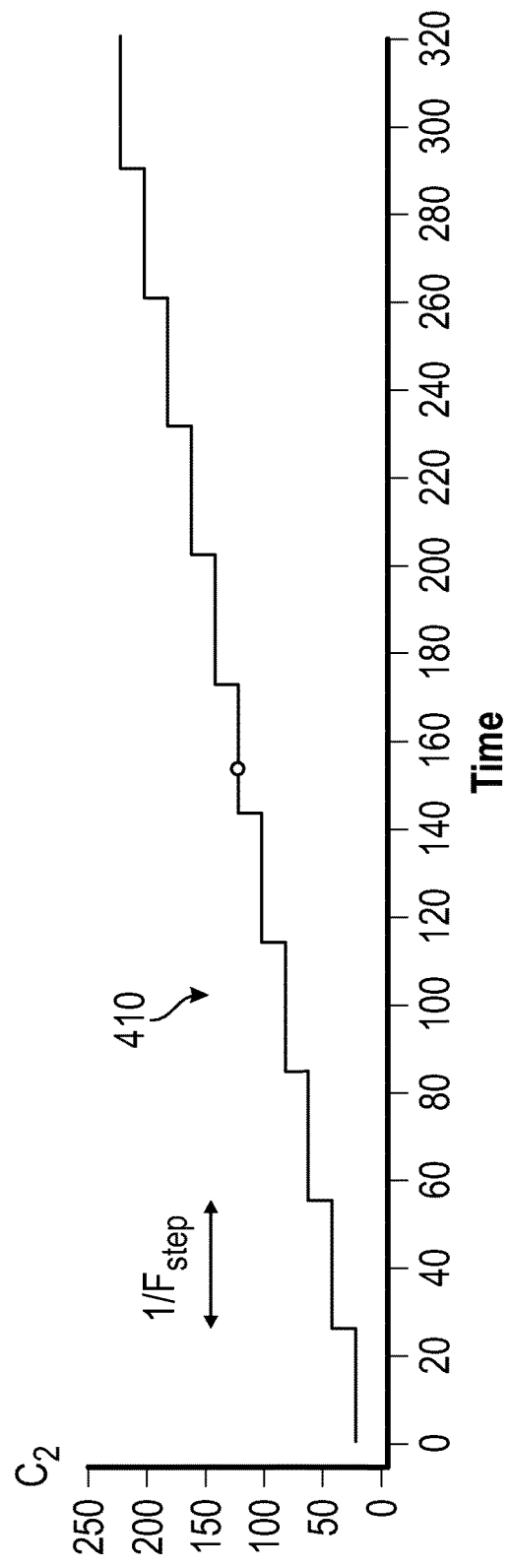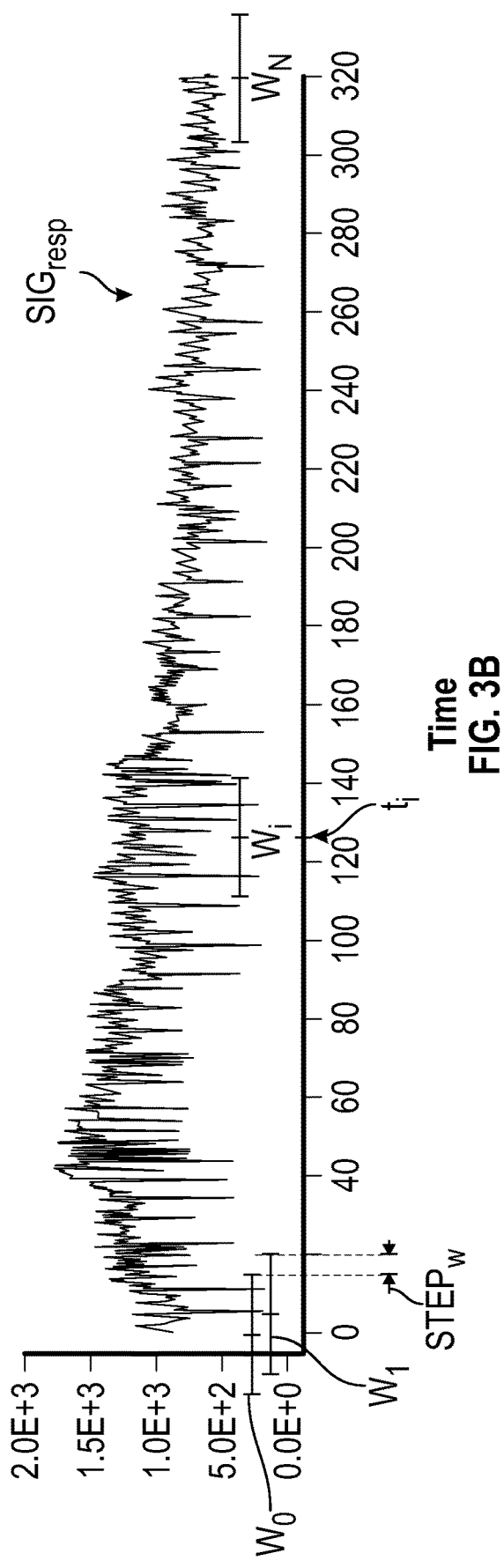
FIG. 3A
FIG. 3B

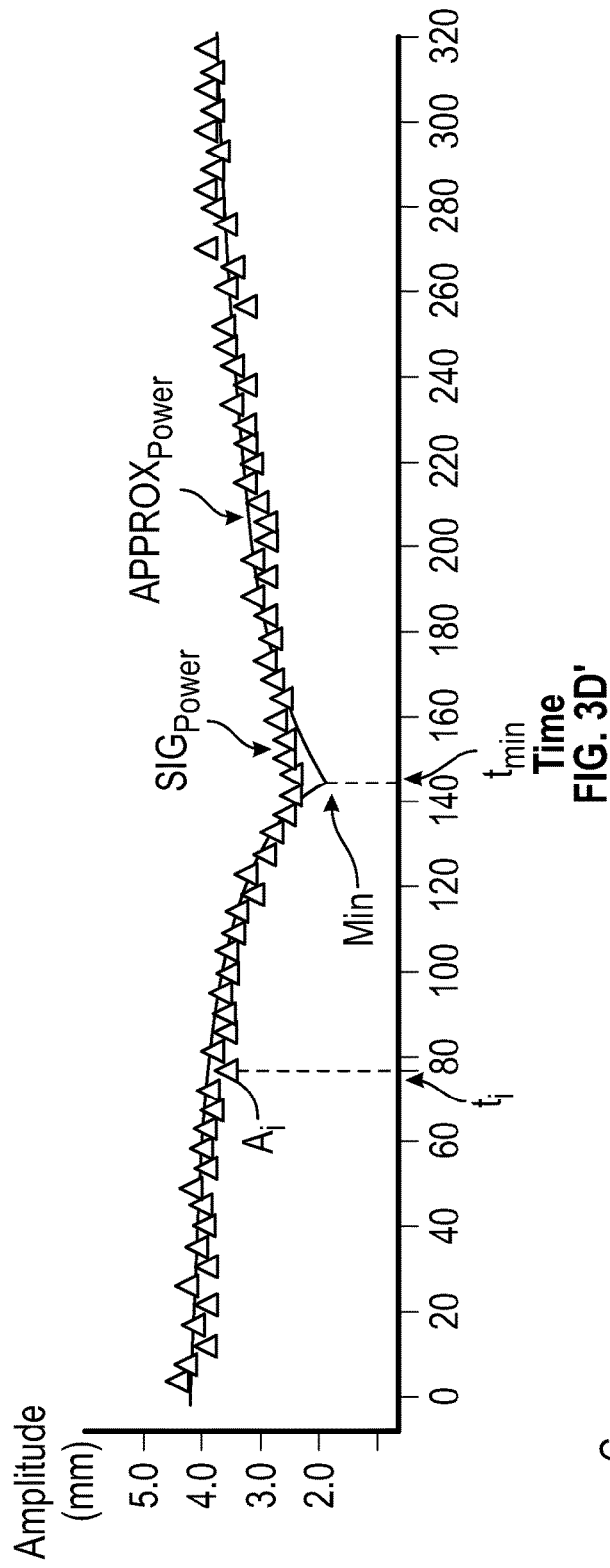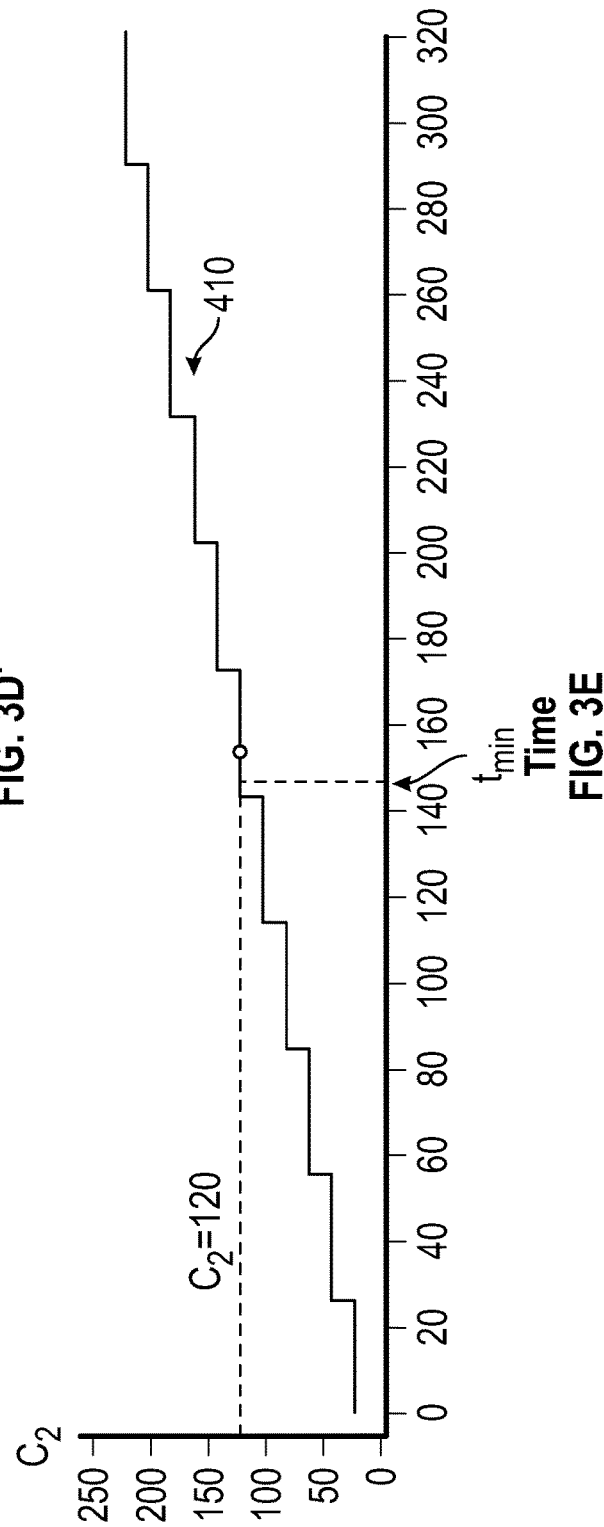

DETERMINATION OF CHROMATIC ISO-LUMINANCE INFORMATION FOR CONTROLLING A COMPUTER PROCESS IN A PERSONALISED MANNER

FIELD OF THE INVENTION

This invention concerns the evaluation of colour perception in mammals, and more particularly a method and system for generating an indicator or biomarker of colour perception in a mammalian subject, such as a human being or an animal. It also concerns the use of such an iso-chromatic luminance type indicator for controlling a computer process in a personalised manner in a computer system.

BACKGROUND OF INVENTION

Colour perception is highly variable from one mammalian subject to another.

This variability is traditionally explained by different concentrations, distributions and sensitivities of chromatic photoreceptors (cones) between subjects in the activated areas of the retina, usually on and around the fovea.

Colour perception changes with the age of the subject.

It is also affected by a dysfunction related to a genetic or acquired pathology of the eye (chromatic photoreceptors), optical pathways or visual brain areas.

Colour perception evaluation is useful for many medical and non-medical applications.

For example, U.S. Pat. No. 5,141,305 describes the evaluation of pure phase neural activity by measuring the pupillary response to an iso-luminant stimulus of a vertical dot or bar pattern whose only displayed colour is alternated between green and red.

An evaluation method, called chromatic iso-luminance, consists in determining when a combination of colours, one of which varies over time, is perceived by the subject as having always (generally twice) the same luminance. This assessment is widely used in psychophysical and neurophysiological studies of visual processing in mammals. In particular, it makes it possible to evaluate the integrity of colour perception in the subject, but also to isolate the relative contribution of luminance-sensitive cells to colour perception.

For a long time, the evaluation of chromatic iso-luminance has remained subjective because it is based on the subjects' perceptual judgements.

To allow objective evaluation in non-verbal mammalian subjects, such as animals and babies, indicators or biomarkers of colour perception in a mammalian subject have been developed. These indicators or biomarkers are in a way objective neurological and physiological signatures of the perception of the colours tested.

The publication "Screening for color blindness using optokinetic nystagmus" (Cavanagh P. et al, 1984) describes, for example, the generation of a signal representative of the nystagmus of the subject's eye in response to an illusory flicker in a grid formed of red and green bars, one of the colours being gradually modified over time. This response signal is an indicator of colour perception in the tested subject. In particular, the iso-luminance between the two colours tested (red and green) is obtained when the direction of movement of the eye reverses in the nystagmus signal.

The publication "A new technique for estimating chromatic isoluminance in humans and monkeys" (Chaudhuri A. et al., 1990) also discloses the generation of an optokinetic response signal to the display of a dynamic bicolour stimulus. A change in nystagmus direction is also used to identify the iso-luminance between the two colours (green and grey) used.

These techniques based on the optokinetic response of the subjects as an indicator of colour perception, however, require a very precise analysis of eye movement. Indeed, involuntary eye oscillations in response to the dynamic bicolour stimulus are generally sudden and rapid.

Sophisticated image acquisition devices (e.g. 100-frame/second cameras) and high-performance processing equipment, especially for real-time processing, are therefore required.

In addition, to guarantee this precision, it is necessary that the subject's gaze does not move. This constraint is difficult to maintain for some subjects, such as animals and babies.

In addition, the use of an oculometer for measuring eye movements requires a calibration procedure for the oculometer. This calibration procedure also requires a response from the subjects, making it difficult to make these measurements precisely with non-cooperative subjects.

There is thus a need for colour perception indicators or biomarkers that are easier to obtain and less constraining.

SUMMARY OF THE INVENTION

The inventors had the idea of relying on the pupil's response to luminance variation. Indeed, since this response (contraction or dilation of the pupil) is slower than nystagmus, the inventors thought that less sophisticated equipment and treatments would then be sufficient.

In this context, the inventors first propose a method for generating an indicator or biomarker of colour perception in a mammalian subject, comprising the following steps of:

submitting the mammalian subject to at least one multi-coloured, typically bicoloured dynamic stimulus comprising displaying, on a display device (screen or other visual medium), a multicoloured, typically bicoloured pattern in which at least two colours are periodically inverted at a so-called marking frequency. The multicoloured pattern thus displays several colours (including the two that are inverted) at any given moment, controlling a change over time of at least one of the two colours of the multicolour pattern when displaying the dynamic multicolour stimulus, to vary the displayed luminance of this colour (usually several times). The purpose of the colour modification is to vary over time the relative luminance between the two colours (i.e. a difference in actual or perceived luminance), acquiring, by using an image acquisition device, an oscillatory response of at least one pupil of the mammalian subject when displaying the dynamic multicoloured stimulus, and generating, from the acquired response, a signal representative of the power of the pupil's oscillatory response as a function of the change over time of at least one of the two colours (and more generally of a difference in luminance between the two colours) when displaying the dynamic multicoloured stimulus.

Classically, the oscillatory response of the pupil consists in measuring the evolution (constriction and dilation) of the pupil diameter over time.

Advantageously, the pupils of both eyes can be analysed separately or in combination (e.g. by way of an average).

Due to the slow oscillatory response of the pupil, the marking frequency used is quite low and, moreover, far from the subject's other physiological frequencies.

Due to this distance from physiological frequencies, the signal-to-noise ratio of the pupil's oscillatory response is naturally low. It then provides a signal representative of the power of the oscillatory response that accurately represents the pupillary response, without contamination. This signal, which is representative of the retinal response and/or perception (specific to the subject) of the colours tested, can therefore be used directly or linked directly to a reliable indicator or biomarker of colour discrimination and/or perception.

The generated signal can then be used in medical or non-medical applications, as discussed below, and for example to determine a chromatic iso-luminance between two tested colours.

In addition, by using a low marking frequency, generally in the range of 0.1 Hz to 5 Hz, for example 1.3 or 1.4 Hz, conventional video acquisition devices, typically 25 frames per second cameras (such as those used on computers and mobile phones), are sufficient. The processing, especially in real time, of the acquired signals is then substantially reduced.

Correlatively, the inventors propose a system for generating an indicator or biomarker of colour perception in a mammalian subject, including:

a display device, a computer system for stimulating the mammalian subject by means of a multicoloured stimulus, typically a two-coloured dynamic stimulus, the computer system controlling the display, on the display device, of a multicoloured, typically a two-coloured pattern, at least two colours of which are periodically inverted at a so-called marking frequency, a colour controller configured to change over time at least one of the two colours of the multicolour pattern when displaying the dynamic multicolour stimulus, to vary the displayed luminance of that colour, an image acquisition device for acquiring an oscillatory response of at least one pupil of the mammalian subject when displaying the dynamic multicoloured stimulus, and an indicator or biomarker generator configured to generate, from the acquired response, a signal representative of the power of the pupil's oscillatory response as a function of the change over time of at least one of the two colours when displaying the dynamic multicoloured stimulus.

This system has similar advantages to the method described above.

Optional method characteristics are also defined later. The system may also include configured means to implement these optional features.

In one embodiment, the method further includes a step of determining the two-colour iso-luminance configuration of the two colours (i.e., the values of these two colours) of the multicolour stimulus, typically a two-colour dynamic stimulus, corresponding to a minimum of the signal representative of the power of the pupil's oscillatory response. The inventors found that due to the periodic inversion of the two colours in the pattern, the pupil oscillates at the corresponding (marking) frequency with a response that is all the more powerful when the perceived intensity differential of the two colours is significant. Also, determining the minimum signal representative of power makes it possible to determine the chromatic iso-luminance perceived by the subject for the two colours tested, i.e. when the difference in luminance that is varied over time between the two colours tested is minimal according to the subject's perception. The correspondence of chromatic iso-luminance can be used as an indicator or marker of colour perception in a subject. Indeed, it can be compared to that obtained for other subjects.

The calculations used to determine the chromatic iso-luminance are excessively simplified compared to known techniques. In addition, the position of the minimum in the signal representative of the power is independent of the unit used to measure the oscillatory response of the pupil. Also, this configuration eliminates the need for calibration of the image acquisition device.

In one embodiment, the other of the two colours of the multicolour pattern is held fixed during the display of the dynamic multicolour stimulus.

In another embodiment, the marking frequency depends on the subject. In particular, the method may also include a preliminary step of determining the marking frequency, including submitting the subject to at least one calibration light flash, measuring an average response time of the mammalian subject's pupil to the calibration light flash, and setting the marking frequency according to the measured average response time.

In particular, these provisions make it possible, at low time cost, to improve the reliability of the measurements taken, for example the configuration of chromatic iso-luminance for the tested colours. In addition, they make it possible to adjust the duration of the test (submission to the multicoloured, typically bicoloured dynamic, stimulus), and in particular to reduce it.

Alternatively or in combination, the multicoloured pattern used depends on the subject, for example on the oscillatory response of the pupil to the light flashes. This makes it possible to take into account any pathology of the subject that alters the spatial sensitivity of the subject's eyes. For example, the multicoloured pattern can be positioned in a preferential area of the screen depending on the subject, for example the top or bottom of the screen, or a particular quarter of the screen.

In one embodiment, the control of the change of colour over time includes a gradual change in increments (or steps). This allows stable oscillatory responses to be acquired, particularly with a sliding analysis window. In particular, a frequency of colour change (in increments) is lower than the marking frequency. Preferably, the colour change frequency is a sub-multiple of the marking frequency. This allows to have several alternations of the same two colours in the multicoloured, typically bicolour, pattern displayed, and thus to acquire a better oscillatory response.

In one embodiment, the mammalian subject is submitted to two multicoloured, typically two-coloured dynamic stimuli based on two different colour pairs. This arrangement provides a complete relative indicator of the subject's colour perception. Indeed, the colorimetric space is generally three-dimensional (for example RGB, for Red-Green-Blue) so that the knowledge of the relative perception of two colour pairs allows to deduce (by simple calculations for example) the relative perception of all colour pairs. This relative perception is for example the correspondence of chromatic iso-luminance.

In one embodiment, the colour display on the display device is controlled using Red-Green-Blue triplets, and the two colours of the multicolour pattern are pure colours for which two of the three components Red, Green, Blue are zero. Thus, the change in time of the colour is done simply by the progressive incrementation of the third non-zero component.

In this case, the two colour pairs indicated above are chosen, in the RGB space, from the pairs RG, RB and GB, where R, G, B are respectively the colours pure red, pure green and pure blue.

The signal representing the power can be formed in different ways depending on the processing applied to the acquired response signal.

In a first embodiment, the signal is a signal representative of the pupil's oscillation power at the marking frequency and/or at one or more of its harmonics, representative of the evolution of the frequency component, at said marking frequency and/or at one or more of its harmonics, of the pupil's oscillatory response. "Harmonic" refers to the multiples and/or sub-multiples of the marking frequency. Typically, in addition to the marking frequency $F_{tag}$, the half-harmonic $F_{tag}/2$ and/or the double harmonic $2*F_{tag}$ can be considered.

The passage in the frequency domain improves the resistance to noise of the indicator or biomarker thus generated. For example, generating the signal representative of the oscillation power of the pupil at the marking frequency involves applying, to the acquired response, a discrete fast Fourier transform over a sliding time window and storing, for each time window, the value of the frequency component at the marking frequency and/or one or more of its harmonics of the obtained frequency spectrum. These processes can be advantageously carried out in real time, with limited memory resources.

In particular, the width of the sliding time window is chosen to be at least equal to the period associated with the marking frequency, for example at least twice that period.

According to another particular characteristic, the sliding time window is shifted by a sample of the acquired response, at each new application of the discrete fast Fourier transform. The temporal accuracy of the samples generally depends on the image acquisition device used and its configuration. Advantageously, the present invention allows the use of a sampling frequency of 25 Hz, corresponding to the definition of a conventional camera (25 frames per second). Thus, thanks to the above provision, the signal representative of the oscillation power generated has the best possible definition taking into account the acquisition device used.

In a particular embodiment, the generation of the signal representative of the oscillation power of the pupil at the marking frequency and/or at one or more of its harmonics further comprises the approximation of a signal formed of the stored values of the frequency component at the marking frequency and/or at one or more of its harmonics by at least one mathematical function, for example a piecewise function which may combine one or more sub-functions among an affine function, an exponential function. Conventional techniques for approximating and selecting each best sub-function for a part of the signal formed from the stored values can be used. The use of such an approximation makes it possible to obtain a relatively simple indicator or biomarker, and thus to simplify subsequent processing, for example the use of this indicator to customize computer operations or to evaluate the evolution of a pathology or the effectiveness of a treatment against such a pathology.

In a second embodiment, the generation of the signal representative of the power involves determining an amplitude of variation of the pupil diameter in response to each inversion of the colours of the multicoloured pattern, typically bicolour, said signal representative of the power being formed from the amplitudes thus determined. These amplitudes, i.e. the differences in pupil diameter at each pupil response, are indeed representative of the power of the pupillary response, within one coefficient (the response time of the pupil).

Any other method that provides a signal representative of the power of the oscillatory response (i.e. the response to each controlled change in the display of the multicoloured pattern) of the pupil can be used.

For all these methods, the analysis can be carried out without any special filtering. Moreover, and advantageously, the present invention allows the use of a sampling frequency of 25 Hz, corresponding to the definition of a conventional camera (25 frames per second). Thus, the signal representative of the oscillation power is generated with the best possible definition taking into account the acquisition device used.

In one embodiment, the method may also include the determination of the minimum signal representative of the power thus generated, for example the minimum of the piecewise function constructed above or the minimum of the signal of the pupil's oscillation amplitudes. This minimum then makes it possible to identify the multicoloured configuration, typically bicoloured, of perceived iso-luminance (or the multicoloured configurations of iso-luminance if, for example, the pattern includes several colour pairs whose luminance of one of them is modified over time).

In one embodiment, the method further comprises a step of filtering the acquired oscillatory response, the filtering step including interpolating, preferably linearly, an oscillatory response signal during a blink of an eye. This allows for the correction of point artefacts in the curve.

The inventors found that the configuration of iso-luminance obtained by the above frequency marking method constitutes an objective and robust signature of the subject.

However, many IT systems require simple and fast access to reliable and robust information from an individual, and in particular from the user, in order to effectively manage IT processes. This is the case, for example, with user identification or authentication processes. Current techniques are complex and sometimes circumventable by stealing user identification information. This is also the case for the configuration of the computer system, which must be adapted to the user as best as possible, for example the calibration of the screen.

Also, the inventors have found that the use of this iso-luminance configuration to control such methods is extremely effective. Thus, this control is made simple, fast, robust, and does not require complex resources.

In this context, the inventors propose a method for controlling a computer process in a personalised manner in a computer system, including the following steps:

determining at least one chromatic iso-luminance information for an individual, as above. That is, determining the iso-luminance information includes the following steps:

submitting the individual to at least one multicoloured, typically two-coloured dynamic stimulus comprising displaying, on a display device of the computer system, a multicoloured, typically two-coloured pattern of which at least two colours are periodically inverted at a so-called marking frequency. The multicoloured pattern thus displays several colours (including the two that are inverted) at any given moment, controlling a change over time of at least one of the two colours of the multicolour pattern when displaying the dynamic multicolour stimulus, to vary the displayed luminance of said colour. The purpose of the colour modification is to vary over time the relative luminance of the two colours (i.e. the difference in perceived luminance), acquiring, by using an image acquisition device, an oscillatory response of at least one pupil of the individual when displaying the dynamic multicoloured stimulus, generating, from the acquired response, a signal representative of the power of the pupil's oscillatory response as a function of the change over time of at least one of the two colours when displaying the dynamic multicoloured stimulus, and determining the two-colour iso-luminance configuration of the two colours in the dynamic multicolour stimulus corresponding to a minimum of the signal representative of the power. This is the value of said two colours obtained when the difference in luminance that is varied over time between these two tested colours is minimal according to the perception of the subject, and using the at least one chromatic iso-luminance information thus determined as the input data of the process into the computer system.

Correlatively, it is also proposed a system for controlling a computer process in a personalised manner in a computer system, including:

a subsystem for determining at least one chromatic iso-luminance information for an individual, and a process control module configured to use the at least one chromatic iso-luminance information thus determined as process input data into the computer system.

The subsystem for determining iso-luminance information includes in particular:

a display device, a computer system for stimulating the individual by means of a multicoloured stimulus, typically a dynamic bicolour stimulus, the computer system controlling the display, on the display device, of a multicoloured, typically bicoloured, pattern, at least two colours of which are periodically inverted at a so-called marking frequency, a colour controller configured to change over time at least one of the two colours of the multicolour pattern when displaying the dynamic multicolour stimulus, to vary the displayed luminance of that colour, an image acquisition device for acquiring an oscillatory response of at least one pupil of the individual when displaying the dynamic multicoloured stimulus, an indicator or biomarker generator configured to generate, from the acquired response, a signal representative of the strength of the pupil's oscillatory response as a function of the change over time of at least one of the two colours when displaying the dynamic multicoloured stimulus, and an iso-luminance determination unit configured to determine the iso-luminance configuration of the two colours in the dynamic multicolour stimulus corresponding to a minimum of the signal representative of the strength.

Optional characteristics of the method for controlling a computer process in a personalised manner are also defined later. The corresponding system may also include configured means to implement these optional features.

The calibration of display screens to obtain a correct perception of colours by the individual (in this case, generally the user) is a complex matter, which generally requires expensive adapted equipment. In 2016, the "True Tone" option was implemented on mobile terminals and tablets from Apple™ or equipped with Android™. This option allows the dynamic adaptation of the white balance, and thus the displayed luminance, to the environmental (lighting) conditions of the display. The perception of colours by users is supposed to be improved, in particular so that these users have the same display and therefore the same perception of the same displayed image when they use different screens.

However, this dynamic adaptation is not satisfactory, as it does not allow different users to have the same perception of the same image on these screens. Indeed, the "True Tone" option is not representative of the user's perception because it does not take into account the sensor (eye) and the processing means (optic nerve, visual brain areas) specific to the user.

In one embodiment, the inventors then considered applying this method to the calibration of a computer system display screen. In this case, the display of a pixel (more generally all pixels) is corrected according to the at least one determined chromatic iso-luminance information. Therefore, this provides a method for calibrating a display screen connected to a computer system, comprising determining chromatic iso-luminance information for a user as described above, and calibrating the colours displayed on the screen according to this determined chromatic iso-luminance information.

This arrangement allows the pixel display to be adjusted to each user so that, regardless of the user, the displayed image has the same perceived luminance between each colour. For example, a perfectly iso-bright image is perceived in this way by each user after personalised manner calibration. Also, several users can work on the same image with the same colour perception while using different screens, sometimes in remote locations.

In one embodiment, the at least one chromatic iso-luminance information comprises, for at least one colour pair among the red-green, red-blue and green-blue pairs of the red-green-blue colour space, a value determined for a first colour when the second colour takes a reference value.

Calibration can be performed by considering a colour as fixed to a reference (e.g. red at (140,0,0)) and using the chromatic iso-luminance green then determined to adjust the display of the green (or red) component on the screen relative to the red (or green).

Preferably, pure colours (two zero components) are used.

In a particular embodiment, for an initial calibration (e.g. by default) of the display screen, a default value of chromatic iso-luminance of the first colour is obtained when the second colour takes the reference value, and the correction of a pixel includes the adjustment (i.e. the modification of the value of the pixel that should have been displayed without personalised manner calibration according to the invention) of the first or second or both colours of the pixel according to the value differential between the default value of chromatic iso-luminance and the determined value of chromatic iso-luminance. For example, if the initial calibration defines an iso-luminance configuration associating the colour red (140,0,0) with the colour green (0,140,0), the determination of an iso-luminance green colour (0,120,0) for the user (for the red-green couple) may lead to a reduction in the green component of the pixels to be displayed on the screen according to the deviation of 20 units thus determined or to an increase in the red component by as much.

A personalised manner chromatic correction of a pixel (or an image) that is easy to implement is thus obtained, to converge towards a perception of the pixel (or image) by this user identical to the perception of the colour by any other user who also benefits from a personalised manner chromatic correction.

According to an optional feature, pixel correction includes modifying the first or second colour of the pixel by a value equal to said value differential. This configuration is extremely simple to implement.

According to a variant, pixel correction involves changing the first colour of the pixel by a value that is a function of both the value differential and the distance of the second colour of the pixel from the reference value.

In particular, this function is preferably linear with respect to said distance between the second pixel colour and the reference value. This allows the correction to be adjusted efficiently so that the modified values remain, without further processing, in the colour space used.

For example, linearity can be determined by the fact that the two ends of the value range (corresponding for example to colours (0,0,0) and (255,255,255)) are invariant points. In this case, the function is piecewise linear on either side of the iso-luminance point determined at the second reference colour.

In one embodiment, the personalised manner control method (or more precisely screen calibration) includes determining two chromatic iso-luminance information for two different colour pairs among the red-green, red-blue and green-blue couples of the red-green-blue colour space, each iso-luminance colour information including a value determined for a first colour when the second colour takes a reference value. This makes it possible to know the user's iso-luminance parameters over the entire colorimetric space considered, here RGB. Also, by these two measurements alone, the invention makes it possible to fully calibrate the display screen so that the user's colour perception is the same as that of another user using a personalised manner calibration according to the same principles.

According to a particular characteristic, the correction of a pixel on the display screen includes the adjustment of a colour triplet (usually RGB) defining the pixel according to an initial calibration of the display screen, based on two value differentials obtained for the two colour pairs, each value differential representing the difference between a default chromatic iso-luminance value for the first colour of the colour pair when the second colour takes the reference value and the determined chromatic iso-luminance value.

Going back to the previous example where the Red-Green iso-luminance measurement for the user gave the configuration of Red (140,0,0)-Green (0,120,0) iso-luminance with therefore a green shift of −20 units. Similarly, an iso-luminance measurement is carried out for the user on the Red-Blue pair resulting in the iso-luminance configuration Red (140,0,0,0)-Blue (0,0,170), with a blue offset of +30 units compared to the default Red iso-luminance configuration (140,0,0)-Blue (0,0,140). The display correction can then consist of increasing the green component by 20 units (or less as the red component moves away from 140) and reducing the blue component by 30 units (or less as the red component moves away from 140).

The identical colour perception by different users is thus easy to achieve.

In one embodiment mode, the adjustment of the colour triplet is performed at constant value of one of its colour components. This configuration limits the calculations to be performed on the components of the pixels to be displayed.

Alternatively, the colour triplet adjustment is performed at constant pixel luminance. This configuration allows to keep the global luminance of an image displayed after personalised manner calibration of the screen according to the teachings of this invention. Generally, the three colour components are adjusted according to the two differentials obtained by the iso-luminance configurations.

Current biometric identification or authentication systems are not sufficiently secure. In particular, the biometric information requested may be reproduced or does not require that the individual whose identity is to be verified, for example, be alive. Therefore, there is a need to improve these biometric identification techniques.

Also, the inventors found that the application of the personalised manner control procedure to such identification/authentication of individuals allows to overcome disadvantages of known techniques. In this method, the process using at least one chromatic iso-luminance information is a procedure for identifying or authenticating the individual, for example with the computer system. This is a method of identifying or authenticating an individual, comprising determining at least one chromatic iso-luminance information for an individual as described above, and using this determined chromatic iso-luminance information as an identifier in an identification or authentication process with the computer system.

Since the chromatic iso-luminance information determined by the invention requires an oscillatory pupillary response from the individual, the individual must be alive to validate the identification or authentication. In addition, it is based on equipment that is not very complex compared to fingerprint or iris sensors.

In one embodiment, the method further comprises comparing the at least one determined chromatic iso-luminance information with at least one corresponding reference chromatic iso-luminance information stored in the memory of the computer system in association with an individual identifier, and the identification or authentication of the individual is only validated if both iso-luminance information match.

In a preferred embodiment, the method comprises determining two chromatic iso-luminance information for two different colour pairs among the red-green, red-blue and green-blue pairs of the red-green-blue colour space, each iso-luminance colour information including a value determined for a first colour when the second colour takes a reference value. This makes it possible to know the individual's iso-luminance parameters over the entire colorimetric space considered, here RGB, and thus to deduce, by simple calculations, any combination of iso-luminance colours necessary for the verification of identification/authentication.

In addition, this verification can then be performed at several points in the colorimetric space, improving the security of access to the computer system.

In one embodiment, the method further comprises a preliminary step of identifying the individual to retrieve the at least one reference chromatic iso-luminance information associated with said individual, before said comparison. Thus, the verification according to the invention using the chromatic iso-luminance configuration(s) is complementary to a more conventional identification. This makes it possible, in particular, to limit the accuracy required in determining this or these chromatic iso-luminance configurations, and thus to reduce the time required for identification/authentication.

For example, the preliminary step of individual identification includes the acquisition of biometric information about the individual, such as a fingerprint or an image of the iris. Alternatively, a simple code/login can be requested.

In one embodiment, the method further comprises determining, according to the identification of the individual thus obtained, at least a limited range (relative to a range of possible values) of modification values to modify over time the colour of the multicoloured pattern, typically bicolour, to be modified when determining chromatic iso-luminance information. For example, identifying the individual whose green iso-luminance value is set at 120 (for a red at 140) can reduce the range of values to be tested to [80-160]. This substantially reduces the amount of data to be acquired, the processing to be performed and thus the time required to acquire the individual's neurological signature.

To enhance system security, this reduced value range can be generated randomly on the fly, as long as it includes the iso-luminance value stored in memory, plus a margin around it. Alternatively, it can be set in the memory of the computer system, in association with the individual's identifier.

BRIEF DESCRIPTION OF THE FIGURES

Other features and advantages of the invention will appear in the following description, illustrated by the attached drawings, wherein:

FIG. 3a illustrates a pattern or profile of modification of one of the colours of the two-colour stimulus pattern of FIG. 2 according to one embodiment;

FIG. 3b represents an example of an oscillatory response of a pupil in response to a dynamic two-colour stimulus of the type shown in FIG. 2 according to one embodiment;

FIG. 3e illustrates the determination of a chromatic iso-luminance value on the modification profile of FIG. 3a according to one embodiment;

DETAILED DESCRIPTION OF EMBODIMENTS OF THE INVENTION

This invention focuses on the perception or discrimination of colours in mammals to make it a biomarker characteristic of each tested subject. It takes advantage of the slow pupillary oscillatory response (between 0.1 Hz and Hz) of a mammalian subject to an oscillatory light stimulus to generate an objective neurological signature of a subject's relative colour perception.

A pupil frequency-tagging method is used at a marking frequency $F_{tag}$ adapted to the pupil response speed, which is advantageously remote from other physiological frequencies associated with the response movements of the subject's eye. For example, $F_{tag}$ is in the range of 1.3 to 1.4 Hz or even less.

This method is robust to noise resulting from other eye movements of the subject and does not require calibration by the subject.

This method makes it possible, for example, to determine the chromatic iso-luminance perceived by a subject from the neurological signature obtained.

Figure 1:
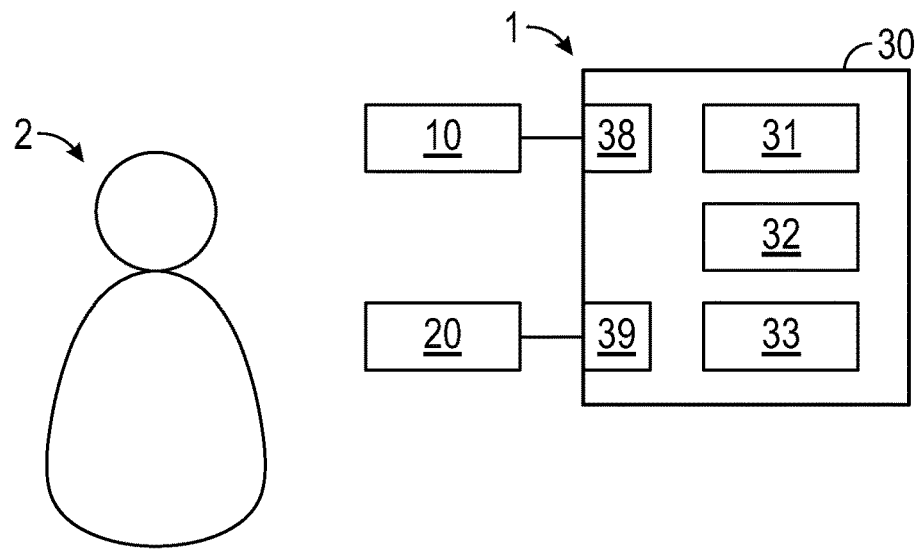
FIG. 1 illustrates a system for generating an indicator or biomarker of colour perception in a mammalian subject according to one embodiment of the invention.

FIG. 1 illustrates a system 1 for generating a colour perception indicator or biomarker in a mammalian subject 2.

It includes a display screen 10, an image acquisition device 20 and a computer system for control and processing 30.

Display screen 10 is a panel of pixels, e.g. of 1920×1080 pixel resolution with a display frequency of e.g. 60 Hz, controlled by a video card from system 30. Each pixel is made up of three colour components of 8 bits each (i.e. can take values from 0 to 255): Red, Green, Blue (RGB). Of course, other pixel definitions (number of bits per colour, colorimetric space) can be considered in the context of this invention.

Screen 10 can be positioned centered facing the subject's eyes, in a plane perpendicular to the gaze, and at a fixed distance from subject 2. To avoid any movement of subject 2, the head of subject 2 can be stabilized by resting the chin and forehead on appropriate supports.

The image acquisition device 20 is typically an infra-red sensitive camera or any type of sensor that records a pupil diameter, also arranged facing the subject so that images of one or more pupils of subject 2 can be acquired.

For simplifying the explanations purposes, the acquisition of images will be limited to a single pupil of subject 2. Of course, similar processings can be performed on the acquisition of images of both pupils, for example averaging or corroborating the results obtained for one pupil with the results of the other pupil, or lastly analyzing the alteration of one pupil relative to the other.

Due to the relatively low marking frequency $F_{tag}$, the use of a camera 20, of the off-the-shelf type, with a speed of 25 frames/second, is possible. In particular, cameras on board conventional electronic devices (mobile phones, computers, digital tablets, portable cameras) can be used as long as they are sensitive to infra-red.

Of course, cameras with acquisition frequencies higher than 25 fps can also be used.

When a camera operates on a frequency spectrum wider than infra-red, filtering (physical or electronic) can be provided using known techniques (and not described here) in order to obtain at the end of acquisition only images in the infra-red spectrum, or at least, allowing to determine the diameter of the pupil observed.

The computer control and processing system 30 includes a computer module for stimulating the mammalian subject by multicoloured stimulus, typically a two-coloured dynamic stimulus 31, a colour controller 32 and an indicator or biomarker generator 33. These various elements are implemented by software because they are essentially processing operations intended to control a display on screen 10 or to process the data acquired by the device 20. For this purpose, the system 30 also includes a conventional video card 38 to which the screen 10 is connected, and a conventional video acquisition card 39 to which the acquisition device 20 is connected.

System 30 may also include input/output means (keyboard, mouse, network card) to allow an operator to configure the system and trigger the invention's methods and applications.

The computer module for stimulating the mammalian subject by a multicoloured stimulus, typically bicoloured dynamic 31, controls the display, on screen 10, of a multicoloured pattern, typically bicoloured, at least two colours of which are periodically inverted at the marking frequency $F_{tag}$.

The multicoloured pattern in question displays several colours at any given time. At least two of these colours are then inverted periodically.

Figure 2:
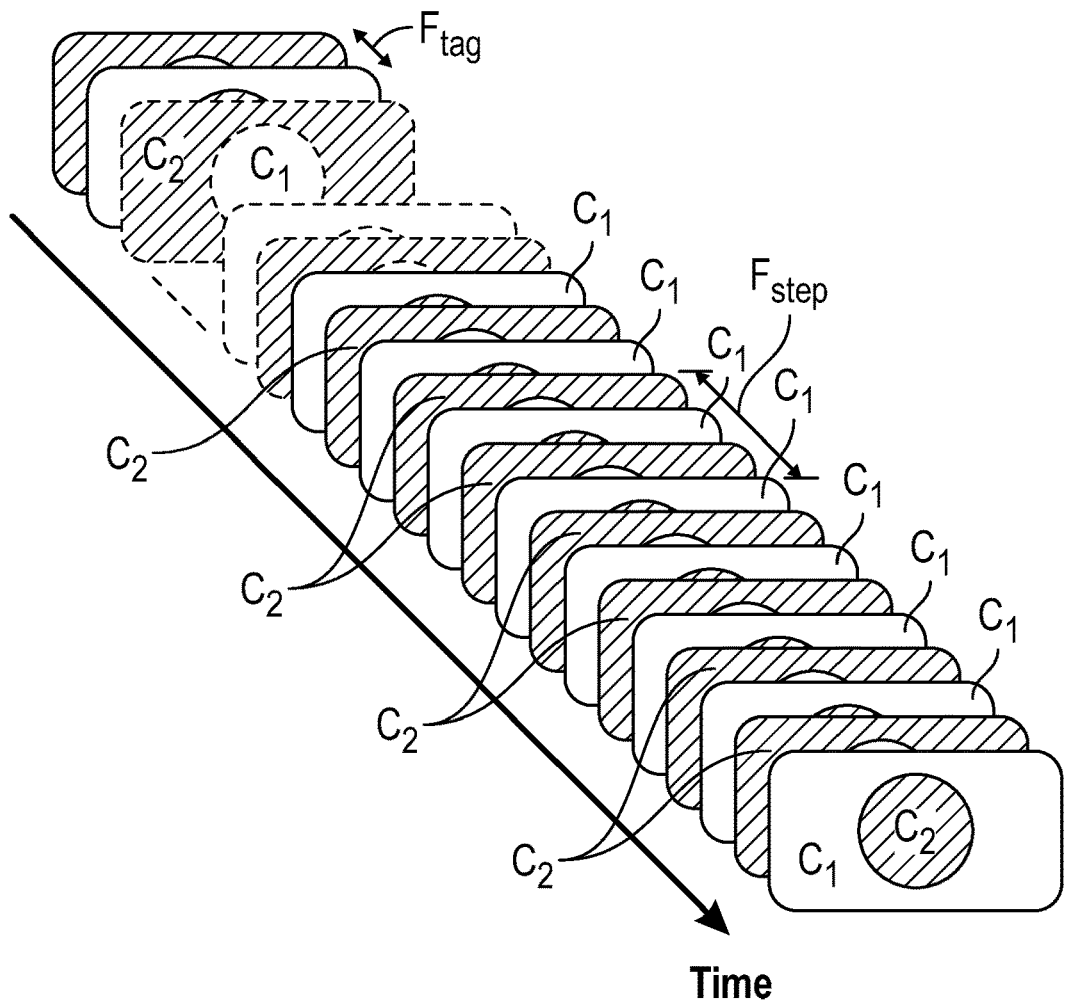
FIG. 2 schematically shows a dynamic two-colour stimulus according to one embodiment of the invention.

FIG. 2 schematically illustrates an example of a two-coloured pattern formed by the colours $C_1$ and $C_2$, a homogeneous background of one of the colours (left in white here for better readability) with, in its centre, a homogeneous circle of the other colour (hatched here for better readability). The dynamic bicolour stimulus consists in creating an alternation between the two colours $C_1$ and $C_2$ at the frequency $F_{tag}$. The two-coloured pattern can be presented on a white background for example.

Preferably, the two colours $C_1$ and $C_2$ of the bicolour pattern are pure colours, i.e. colours for which two of the three components Red, Green, Blue are zero. In the colorimetric space RGB, $C_1$ and $C_2$ are thus either RG, RB or GB, where R, G, B are respectively the pure colours red ($r_i$,0,0), green (0,$g_i$,0) and blue (0,0,$b_i$).

Note that $C_1$ and $C_2$ can be chosen as the same pure colour (RR, GG, BB), especially for control tests. Of course, other choices of colour pairs ($C_1$, $C_2$) not necessarily involving pure colours can be considered.

The colour controller 32 is configured to change over time at least one of the two colours of the multicolour pattern, typically bicolour (FIG. 2) when displaying the multicolour stimulus, typically dynamic bicolour, on screen 10, to vary the displayed luminance of this colour (usually several times). For pure colours, the luminance variation is easy to obtain, simply by modifying the only non-zero component ($r_i$ or $g_i$ or $b_i$).

The aim of this modification of one of the two colours is to vary over time the relative luminance between the two colours considered, i.e. to vary a difference in luminance between these two colours, a difference that is real or perceived by the subject.

In one embodiment, the other colour of the pattern, say $C_1$, is held fixed during the display of the dynamic two-colour stimulus. This means that throughout the test (all the images displayed in FIG. 2), colour $C_1$ is displayed with the same RGB triplet. Of course, this other colour can also be changed over time (for example in the opposite direction to the first colour).

What is important here is to determine the offset between the two colours that ensures perceived iso-luminance. As a first approximation, this offset can then be applied to any value of one of the colours, to obtain the value of the other colour in iso-luminance configuration.

The change in time of the colour $C_2$ is preferably carried out in increasing steps in a range of possible values (e.g. from 0 to 255 for the modified component alone) or in a range of values to be tested, or in decreasing steps (e.g. from 255 to 0) during the test. For non-pure colours, the resulting luminance (different formulas from the RGB components are available to the skilled person) will be chosen increasing or decreasing during the test.

Alternatively, a modification of the colour $C_2$ by dichotomy around a first iso-luminance value determined in a first test (based on the techniques of this invention or other methods) may be considered.

Other examples of multicoloured patterns can be used, for example including a larger number of colours or a multicoloured pattern displaying two or more different pairs of colours that are inverted two by two as explained above, for example. Also, spatially different patterns may be considered in the display area on screen 10, for example a display on either quarter screen or a display on the upper (or right) or lower (or left) part of the screen.

To simplify the following explanations, reference is made mainly to a two-coloured pattern whose two colours displayed simultaneously are inverted (which can for example be displayed on a uniform background, ultimately resulting in a multicoloured display).

FIG. 3a illustrates an example of controlling the change of colour $C_2$ over time by gradually changing it in increments (or steps). The difference in luminance between the two colours thus varies over time. In this example, the non-zero component of colour $C_2$ is varied between 20 and 220 (the extremes are not significant), in steps of 20 units. Of course, other tested ranges, with other steps, can be used to reduce or extend the test time, but also to reduce or improve the accuracy of the determination of, for example, chromatic iso-luminance.

In particular, a higher accuracy (narrower range and smaller steps) may be used in a second test around an approximate iso-luminance value (i.e. the value of $C_2$ having the same luminance perceived by subject 2 as the fixed value of $C_1$) previously determined in a first test (based on the techniques of the present invention or other methods).

As shown in FIG. 2, the frequency $F_{step}$ of $C_2$ value increment is chosen lower than the marking frequency $F_{tag}$, for example 3 times lower (FIG. 2—meaning that three consecutive displayed images have the same $C_2$ colour value), about 10 times lower (FIG. 3a) or more, or possibly a sub multiple of $F_{tag}$.

Figure 3C:
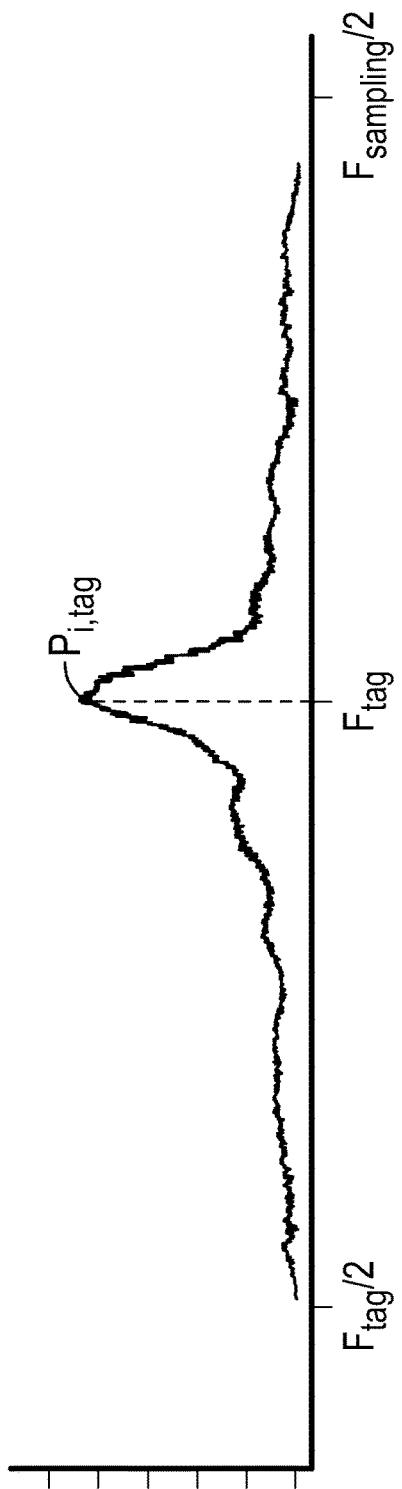
FIG. 3c schematically illustrates a frequency spectrum resulting from the application of a discrete fast Fourier transform to a signal analysis window of FIG. 3b according to one embodiment.
Figure 3D:
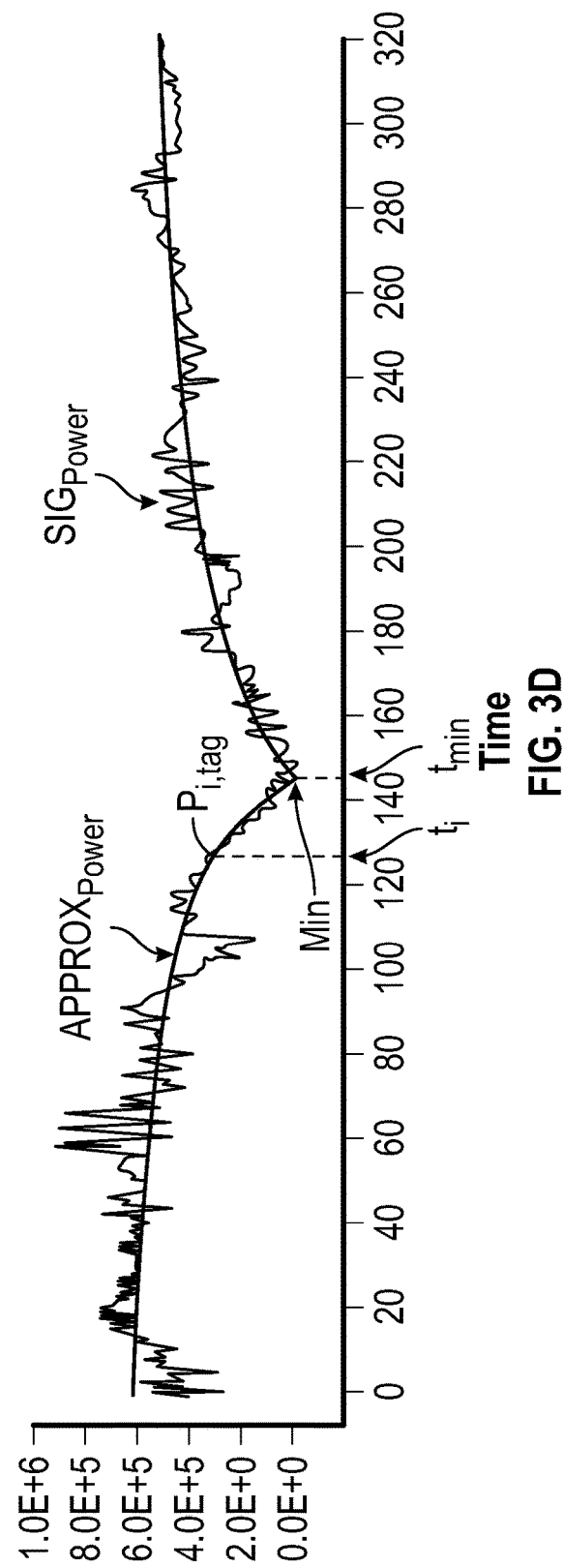
FIGS. 3d and 3d' illustrate signals representative of the pupil's oscillation strength, and a piecewise function approximating them, according to different embodiments.

Referring again to FIG. 1, the indicator or biomarker generator 33 is configured to generate, from an oscillatory response $SIG_{resp}$ of at least one pupil of subject acquired by the acquisition device 20, a oscillation strength signal $SIG_{power}$ of the pupil. An example of an oscillatory response is shown in FIG. 3b, while examples of pupil oscillation power signals are shown in FIGS. 3d and 3d'.

This signal $SIG_{power}$ is representative of the power of the pupil's oscillatory response as a function of the change over time (FIG. 3a) of at least one of the colours when displaying the dynamic two-colour stimulus.

Different embodiments can be considered to obtain this $SIG_{power}$ signal,

A first quick method consists in determining an amplitude $A_i$ of variation in pupil diameter in response to each inversion (at $t_i$) of the colours of the bicolour pattern. Each amplitude $A_i$ quantifies the change in pupil diameter during pupillary response. Such an amplitude is representative of the power of the pupillary response, within one coefficient (the response time of the pupil). The signal $SIG_{power}$ is then formed from the amplitudes thus determined (see FIG. 3d' in which the triangles schematically represent each amplitude $A_i$ ($t_i$) determined).

A second method that is more resistant to noise is to work in the frequency domain of the oscillatory response $SIG_{resp}$. In this case, the signal $SIG_{power}$ is preferably a signal representative of the oscillation power of the pupil at the marking frequency, representative of the evolution of the frequency component $P_{i,tag}$, at said marking frequency $F_{tag}$, of the oscillatory response $SIG_{resp}$ of the pupil as a function of the change over time (FIG. 3a) of the colour $C_2$ when displaying the dynamic bicolour stimulus (FIG. 2). The signal $SIG_{power}$ is then formed by the frequency components $P_{i,tag}$ thus determined (see FIG. 3d).

It should be noted that the determination of these frequency components does not necessarily require the acquisition of the complete oscillatory responses to each colour inversion. Indeed, known techniques allow these frequency components to be obtained from a partial cycle of the pupil's oscillatory response. In a preferred embodiment, complete oscillatory responses are relied upon.

Alternatively or in combination with the first harmonic $F_{tag}$, it is possible to focus on the harmonics of the marking frequency $F_{tag}$, in particular sub-harmonics such as the half-harmonic $F_{tag}/2$ and/or multiple harmonics such as the double or second harmonic $2*F_{tag}$. In this case, each harmonic is treated separately as described below, their results can be combined (by means of an average or to adjust the result of the first harmonic, etc.) to obtain a unique two-colour configuration of iso-luminance.

Thus, from the signal $SIG_{power}$ of any processed harmonic, the indicator generator or biomarker 33 can determine the iso-luminance of $C_2$ with respect to $C_1$ (fixed). As explained later in reference to FIG. 4 in connection with FIGS. 3d and 3e, this chromatic iso-luminance corresponds to the bicolour iso-luminance configuration of the dynamic bicolour stimulus corresponding to a minimum of the signal $SIG_{power}$. Indeed, the amplitude of the pupillary response and therefore its oscillation power closely follow the variations in the luminance of the displayed stimulus. They are therefore minimal when the variations in luminance are minimal, i.e. when the chromatic iso-luminance perceived by the subject of the displayed bicolour pattern is minimal.

Figure 4:
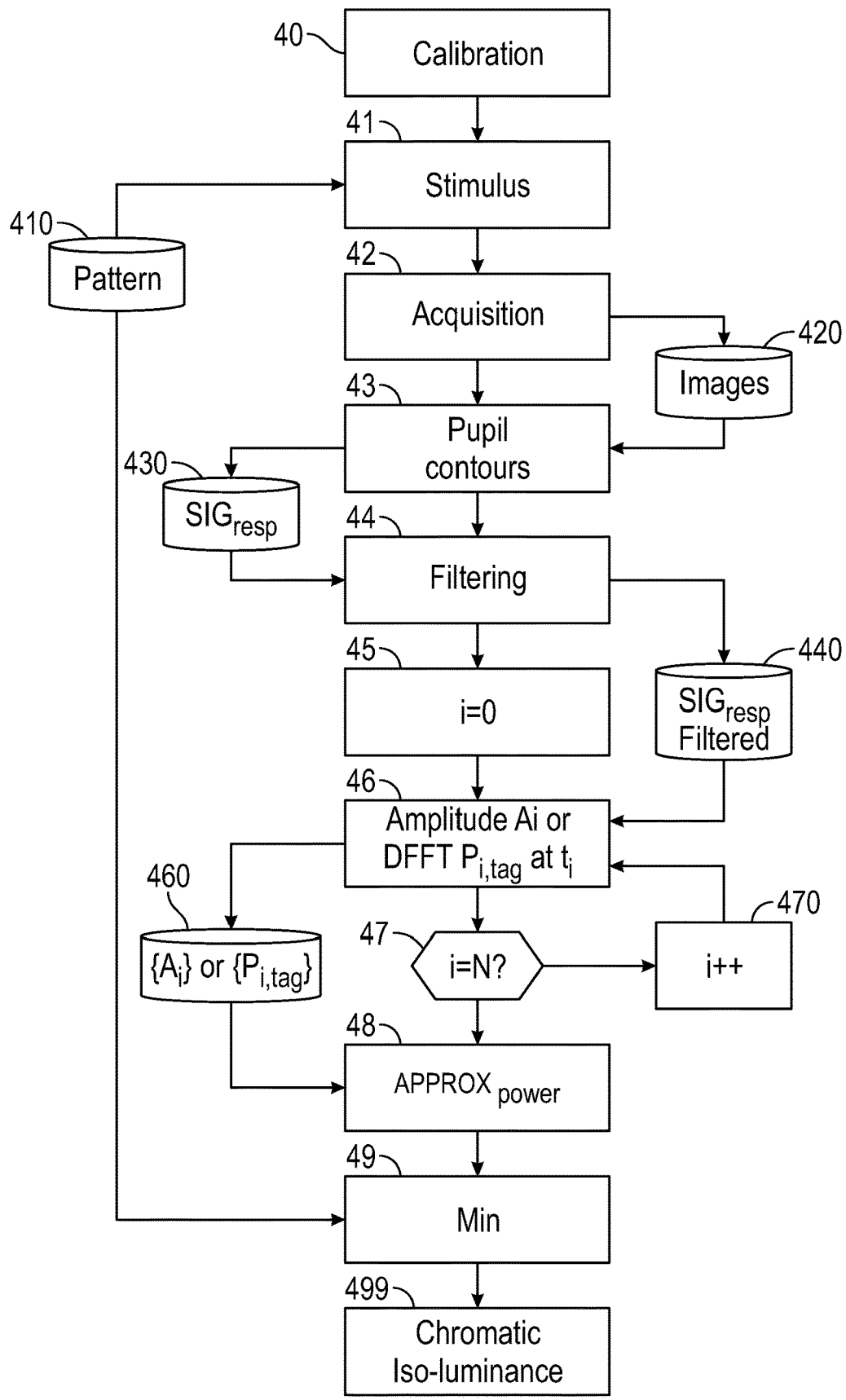
FIG. 4 illustrates, by means of a flowchart, a method for generating an indicator or biomarker of colour perception in a mammalian subject according to embodiments of the invention.

With reference now to FIG. 4, an example of a process for generating an indicator or biomarker of colour perception in a mammalian subject according to the teachings of this invention is described.

When starting system 1, an optional step 40 allows the system 1 to be calibrated to the subject 2 being tested. In particular, this step aims to determine the frequency $F_{tag}$ according to subject 2 and/or the pattern to be used. Indeed, pupillary response time varies, sometimes greatly, from one subject to another. Also, to reduce the duration of the test or to ensure relevant measurements, it is preferable that $F_{tag}$ is as large as possible while avoiding that it exceeds the subject's pupillary response speed.

In addition, a spatially differentiated pattern in relation to the subject's fixation point may be considered in order to isolate conditions specifically affecting certain areas of the subject's retina. For example, a difference in colour perception may exist for patients with Alzheimer's disease, while particular areas are difficult to perceive by patients with localized AMD (these areas correspond to the degenerating parts of the retina due to the pathology).

Calibration step 40 generally consists of recording the subject's pupillary response (usually in constriction), to derive a pupillary response time and thus a frequency $F_{tag}$ to be used (e.g. using a correspondence table), and/or a subject's sensitivity area defining a preferential area for displaying the two-colour pattern.

For example, subject 2 may be submitted to at least one calibration light flash controlled by system 30 and displayed on screen 10 (for example, a sudden white screen from a dark screen or a sudden white area in the dark screen, the location of this white area may vary during the calibration test).

An acquisition, by device 20, of the images of the pupillary response(s) of subject 2 (flash or multiple flashes) makes it possible to obtain a signal representative of the variation (constriction) of the pupil (in particular its diameter), from which the response time (possibly average over several responses) of the pupil can be measured by conventional techniques (for example the time taken, starting from the flash, to reach 90% of the response constriction). Typically, an individual's pupillary response time is in the range of 0.5 seconds to 2 seconds.

From this measured or calculated response time, step 40 determines the frequency $F_{tag}$. This can be done using a mapping table (which associates respective $F_{tag}$ values with response time ranges) in order to have a limited number of marking frequency values. In variance, the period associated with the marking frequency $F_{tag}$ can be set to double the response time or to another multiple of the measured response time.

By default, a $F_{tag}$ value of about 1.3 to 1.4 Hz can be used.

Also from pupillary responses to the display of a flash in several areas of the screen, while the subject retains a fixing point, the device determines an area of greater sensitivity of the subject. This field can then be used to display the two-colour pattern on only part of the screen. Also, spatially differentiated patterns are finally displayed according to the subjects concerned.

In step 41, subject 2 is subjected to at least one multicoloured stimulus, typically bicoloured dynamic.

Although the following description focuses on the subject's being submitted to a single bicolour stimulus, it may be planned to successively submit it to two successive dynamic bicolour stimuli based, for example, on two different colour pairs, in order to obtain a relative perception of the subject's colours over the entire three-dimensional RGB colour space. For example, a test determining the chromatic iso-luminance of the RG couple for the subject can be combined with a second subsequent test determining the chromatic iso-luminance of the GB couple. The relative perception between the Red and Blue colours can then be deduced directly, so that the relative perception of all colours in the colorimetric space is known for the subject.

Also, although the stimulus used here is bicoloured in the sense that only two colours are inverted, at least one of them varying over time, it can be expected that the multicoloured stimulus used includes several different pairs of inverted colours at the frequency $F_{tag}$, displayed simultaneously on the same screen.

In step 41, the computer module for stimulating the mammalian subject by dynamic bicolour stimulus 31 controls the display of the bicolour pattern possibly in a preferential display area and the periodic inversion of the two colours $C_1$ and $C_2$ at the frequency $F_{tag}$ (FIG. 2). At the same time, the luminance of colour $C_2$ is changed over time according to a modification profile 410, under the control of colour controller 32. The modification profile can be incremental as shown in FIG. 3a for the non-zero component of $C_2$.

In step 42, the image acquisition device 20 films and acquires images, in the infra-red spectrum, of the monitored pupil of subject 2. These images are transmitted to system 30 and stored in memory 420. The acquisition is performed at a sampling rate $F_{sampling}$ of 25 to 1000 frames per second, depending on the capabilities of the device 20.

In step 43, the acquired images are processed using an algorithm for detecting pupil contours and measuring pupil diameter. These measurements make it possible to establish an oscillatory response signal $SIG_{resp}$ of the pupil during the display of the dynamic bicolour stimulus, representing the evolution of the pupil diameter over time.

FIG. 3b illustrates an example of the pupil's oscillatory response $SIG_{resp}$ to a bicolour dynamic stimulus Red-Green, whose pure red colour is set at (140.0.0) and the pure green colour follows the curve in FIG. 3a ($F_{step}$=0.0345 or steps of about 29 seconds). The frequency $F_{tag}$ is set at 0.345 Hz.

The resulting $SIG_{resp}$ curve is stored in memory 430 of system 30.

It should be noted that the contour detection and $SIG_{resp}$ generation processes can be embedded in the acquisition device 20 in order to reduce the volume of data to be transmitted to the computer system 30.

The oscillatory response $SIG_{resp}$ can be used as such in steps 45 to 49 described below. Indeed, the use of the frequency $F_{tag}$, far from the physiological noise frequencies, guarantees a good robustness of this response.

However, it may be possible, as an option, to filter this response in order to remove artefacts in the signal.

In this case, the method continues at the optional step 44 of filtering the acquired oscillatory response $SIG_{resp}$. One of the aims of this filtering is to remove noise in the signal (for example noise resulting from a blink of the eye where no pupils could be detected by the contour detection algorithm).

In one embodiment, step 44 consists in interpolating, preferably in a linear way, the oscillatory response signal $SIG_{resp}$ during one or more eye blinks, i.e. when the contour detection algorithm could not detect a pupil in the images. Traditional interpolation techniques can be used.

For example, filtering based on the Savitzky-Golay method can be implemented.

The filtered signal is stored in memory 440 of system 30.

It is from this filtered or unfiltered signal $SIG_{resp}$ that the signal $SIG_{power}$ is generated.

In the first embodiment mentioned above, generator 33 can determine the times t of colour inversion in the displayed bicolour stimulus, then determine in each corresponding oscillatory response, the amplitude $A(t_i)$ of the variation in pupillary diameter of subject 2.

It may simply be a matter of determining the difference between the diameter value at the time of the colour inversion and the opposite end value (maximum or minimum) of the diameter in a time window corresponding substantially to the subject's response time.

Of course, other methods of amplitude evaluation can be considered, such as using a percentage of the end value of the diameter or the value of the diameter at 90% (or less) of the response.

All the calculated amplitudes, associated with the respective times of colour inversion, form the signal $SIG_{power}$ (FIG. 3d) used in steps 48 and 49 below.

In the second embodiment based on the frequency domain, the obtained signal $SIG_{resp}$ (possibly filtered) is transformed into the spectral domain to analyze the evolution of the frequency component $F_{tag}$ and/or its harmonics. To do this, a discrete fast Fourier transform (DFFT) is applied to the signal $SIG_{resp}$ over a sliding time window $W_i$. This results in a frequency spectrum corresponding to the portion of the signal analysed by the window. Then, for each analysis time window $W_i$, the value $P_{i,tag}$ of the frequency component at the frequency $F_{tag}$ (and/or one or more harmonics) is stored.

The following description focuses on the frequency component $F_{tag}$. A similar approach can be used to deal with any harmonic of interest.

FIG. 3b shows the analysis time windows $W_i$ used from the first window $W_0$ to the last window $W_N$. To ensure the presence of the frequency component at $F_{tag}$ in the spectrum, the width of the sliding time window $W_i$ is at least equal to the period $T_{tag}$ associated with the marking frequency $F_{tag}$. In the example in the figure, for example, a width equal to $2*T_{tag}$ (or greater) is selected. Thus, from the window $W_0$, centered on $t_0$, a non-zero component $P_{0,tag}$ can be obtained.

Each analysis window $W_i$ is centered on (therefore associated with) the time $t_i$. Preferably, a window $W_i$ is associated with each sampling time, in order to obtain the maximum resolution of the signal representative of the oscillatory power formed by the values $\{P_{i,tag}\}$. In this case, the sliding time window $W_i$ is shifted by a sample of the acquired response $SIG_{resp}$ with each new application of the fast Fourier transform. Of course, the step $STEP_W$ of shifting the analysis window W can be greater than a single sampling period ($T_{sampling}$=$1/F_{sampling}$ used in this example). A step $STEP_W$ set to several sampling periods reduces calculations and the memory size required.

To obtain a signal representative of the oscillation power $SIG_{power}$ of the pupil at the frequency $F_{tag}$ representative of the evolution of the frequency component $F_{tag}$ of the pupil's oscillatory response $SIG_{resp}$, the process can first include initializing a variable T to zero (to process each sample) in step 45.

Then, the DFFT is applied to the portion of the signal $SIG_{resp}$ signal defined by the current time window W, centered on the sample T to be processed (i.e. $t_i$). FIG. 3c illustrates a schematic example of the resulting frequency spectrum. Note the absence of frequency components below the frequency corresponding to the width of the W window, and above the half frequency sampling (Nyquist criterion). Harmonic components of $F_{tag}$ may therefore be present.

This graph shows that the frequency component $P_{i,tag}$ at $F_{tag}$ has an excellent signal-to-noise ratio, because $F_{tag}$ is far from the physiological frequencies of subject 2, which may be parasitic. The $P_{i,tag}$ value is obtained and stored in memory 460. This is step 46.

It is understood that the DFFT, since it operates on discrete values (samples), does not necessarily produce a frequency component exactly at the frequency $F_{tag}$. Also, the $P_{i,tag}$ value can be that of the frequency component obtained closest to $F_{tag}$, or an approximation (linear for example) between the two (or more) frequency components surrounding $F_{tag}$, or an average of two or more frequency components surrounding $F_{tag}$.

Note that using as large a sampling frequency $F_{sampling}$ and/or window size W as possible increases the number of frequency samples in the spectrum, especially around $F_{tag}$.

After step 46, it is determined if all the DFFTs have been performed (test 47 verifying that i=N, number of samples to be processed over the test period), otherwise the variable "i" (step 470) is incremented to perform the signal DFFT on the next window W.

When the DFFT has been applied using all windows (i.e. on all pieces of the response $SIG_{resp}$), memory 460 stores all the $P_{i,tag}$ values that together form the signal $SIG_{power}$ from the pupil to the frequency $F_{tag}$ (see FIG. 3d).

The signal $SIG_{power}$ generated by any of the methods is already an indicator or biomarker of colour perception in subject 2. It is indeed a robust neurological signature of subject 2. As we will see later, analysis of its evolution over time can make it possible to detect a pathology or a worsening of a pathology. This is the case, for example, with multiple sclerosis.

Optional steps 48 and 49 allow this indicator or biomarker to be refined. The general shape of the signal $SIG_{power}$ shows a lower central area than the lateral areas.

In optional step 48, an algorithm for approximating the signal $SIG_{power}$ is implemented in order to match this signal to a mathematical function. In particular, it is tried to match the signal to a piecewise function, where each piece can correspond to an affine function, an exponential function or any other conventional function.

In the example in FIG. 3d, an exponential function per piece (two pieces) $APPROX_{power}$ is used to correspond to the generally decreasing part of the signal (left) and the generally increasing part of the signal (right). Conventional mapping approximation techniques can be used, without having to detail them here.

The signal $APPROX_{power}$ thus obtained can also be used as an indicator or biomarker of colour perception in subject 2.

Step 49 then consists in determining the $C_2$ value of the colour $C_2$ that minimizes the signal $SIG_{power}$ or its approximation $APPROX_{power}$—This involves determining the minimum MIN of the $SIG_{power}$ or $APPROX_{power}$ signal, using conventional techniques and determining the value of $C_2$ at the instant train corresponding to this minimum signal, using the modification profile 410 (FIG. 3a as reproduced in FIG. 3e).

In this example, the value $C_2(t_{min})=120$ is obtained for $C_2$. In other words, subject 2 perceives a relative chromatic iso-luminance between the pure red and green colours for the values $C_2=(140.0.0)$ and $C_2=(0.120.0)$ for the example shown.

The resulting configuration of iso-luminance 499 can be used as an indicator or biomarker of colour perception in subject 2.

This configuration can be combined with one or more other corresponding iso-luminance configurations determined from one or more harmonics of $F_{tag}$.

It should be noted that in the case where the dynamic multicolour stimulus used has several different colour pairs that are inverted at the frequency $F_{tag}$, the minimum MIN of the $SIG_{power}$ or $APPROX_{power}$ signal corresponds to an overall iso-luminance configuration of the different colour pairs, without this configuration specifically corresponding to an iso-luminance configuration of each colour pair taken separately.

In one embodiment, the configuration of iso-luminance obtained can be confirmed by reproducing the test with an inverse modification profile 410 (decreasing in steps from 220 to 20, for example). In particular, an average of the two c2 values obtained in these two tests can be calculated to represent the average iso-luminance configuration of subject 2 for colours $C_1$ and $C_2$.

The above method was tested on 4 human subjects over sessions of 45 minutes each and 7 non-human mammalian subjects over one session of 20 minutes. The marking frequency chosen was 0.345 Hz, adapted to all the subjects studied. The bicolour pattern used was that of FIG. 2, with one fixed colour and the other varying stepwise (as shown schematically in FIG. 3). The flat screen 10, with a 1920× 1080 pixel resolution, 8 bits per colour, 60 Hz was fixed at a distance of 67 cm from the subjects.

The inventors observed, for all subjects, a maximum reduction in the power of pupillary oscillations induced by the variations in luminance of the stimulus to the iso-luminance configuration of the bicolour pattern tested.

The inventors found that this method of obtaining an iso-luminance configuration, a user's personal signature, has undeniable advantages for the personalised manner control or monitoring of IT processes.

FIGS. 5 to 8 illustrate several ways of carrying out such a personalised manner control, and consequently several applications of the iso-luminance configuration in fields that are not necessarily medical.

Generally speaking, the personalised manner control of a process in a computer system, according to the invention, includes the following steps:

determining at least one chromatic iso-luminance information for a user of the computer system using the teachings given above, for example the procedure in FIG. 4. In particular, an iso-luminance configuration of the multicoloured stimulus, typically two-coloured dynamic stimulus, is determined corresponding to a minimum of the signal, in particular $SIG_{power}$; and using the at least one chromatic iso-luminance information thus determined as input data of the process into the computer system.

Figure 5:
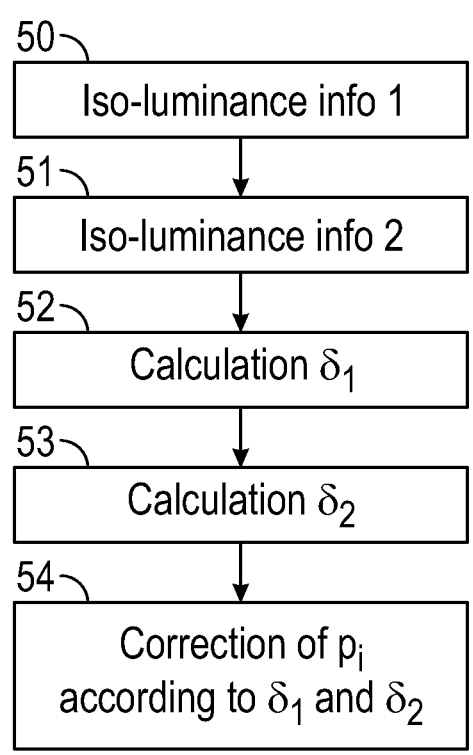
FIG. 5 illustrates, by means of a flowchart, a method of calibrating a display screen using the iso-luminance information type indicator or biomarker determined by the method of FIG. 4, according to embodiments of the invention.

FIG. 5 illustrates the application of the iso-luminance configuration to the calibration of a computer system display screen. For example, screen 10 (FIG. 1) may be calibrated for user 2, allowing him to display an image and perceive its colours in the same way as another user would on the same image with another screen calibrated using the same techniques.

An advantage of this method is that it can be implemented on consumer digital systems with medium resolution cameras: computer monitors, laptops, digital tablets, smartphones, etc., to calibrate their displays. It does not require complex components.

The illustrated method includes, in step 50, the determination of a first iso-luminance information, using for example the process in FIG. 4. Typically, a colour pair among the red-green, red-blue and green-blue pairs of the red-green-blue colour space is considered. Step 50 provides a value determined for a first colour (e.g. green) when the second colour (e.g. red) takes a reference value e.g. $r_{ref}=140$ (corresponding to Red (140,0,0)). The value determined, for example $g_2=120$ for colour (0,120,0) in the above example, is thus the first iso-luminance information.

In optional step 51, a second iso-luminance information can be obtained by also using the process in FIG. 4 for example. This second information can be obtained for another colour pair, for example red-blue in an example given above for which the value Blue=(0,0,170) is obtained for the reference red (140,0,0).

Thus, two chromatic iso-luminance information, for example $g_2=120$ and $b_2=170$, are obtained for two different colour pairs among the red-green, red-blue and green-blue couples of the red-green-blue colour space. Each chromatic information of iso-luminance includes a determined value, $g_2=120$ and $b_2=170$, for a first colour (green and blue respectively) when the second colour (red in both cases) takes a reference value $r_{ref}=140$ for Red (140,0,0).

In this example, the colours used are preferably pure.

In step 52, a differential 8i of value is calculated, the first $g_2$ value obtained and a corresponding calibration default value (here from the green component). Indeed, the idea in this case is to correct the default calibration of screen 10.

This gives the initial calibration parameters of display screen 10. These parameters can be in system memory or provided by a controller (not shown) on screen 10. These parameters allow to obtain a $g_{default}$ value by default of chromatic iso-luminance of the first colour, in this case green, for screen 10 when the second colour, in this case red, takes the reference value $r_{ref}$=140 for Red (140,0,0). To simplify the explanations, let's assume that the initial iso-luminance calibration of screen 10 is (140,140,140), meaning that all colour components are isoluminant.

Step 52 then consists in calculating $\delta i = g_2 - g_{default}$.

In the example, $\delta_1 = 120 - 140 = -20$.

Note that if step 50 does not provide a chromatic iso-luminance value to the reference value (in this case red) considered in the calibration parameters, an adjustment can be provided (for example, by addition/subtraction of the same number of units for both colours of the determined iso-luminance configuration, so that the second colour takes the reference value).

The optional step 53 is similar, for the calculation of a differential $\delta_2$ of value the second value $b_2$ obtained and a corresponding calibration default value (in this case of the blue component).

In the example, $\delta_2 = b_2 - b_{default} = 170 - 140 = +30$.

It should be noted that the iso-luminance configuration for the third untreated colour pair can be determined directly from the two configurations obtained in steps 50 and 51. In the example, the configuration of the green-blue iso-luminance must represent, for example, the $b_2$ value of the blue iso-luminance perceived by the user when the green is set to the reference value 140. The configurations show that at constant luminance, green is 20 units weaker than red, itself being 30 units more stronger than blue. Also, the iso-luminance value $b_2$ is 190 for a reference green set to (0,140,0).

The process continues with step 54 by using this or these differential(s) to adjust the calibration of screen 10. In particular, the display of a pixel (more generally all pixels) is corrected according to the determined chromatic iso-luminance information $g_2$ and/or $b_2$, for example the colour triplet (usually RGB) defining the pixel is adjusted according to an initial calibration of the display screen according to the two differentials $\delta_1$ and $\delta_2$.

Different variants of the colour correction ($r_i, g_i, b_i$) of a pixel Pi of the screen can be considered. After correction, the colours are noted ($r_{new}, g_{new}, b_{new}$).

Some variants operate at constant value of one of its colour components. Let's take the example of the red component r, unchanged (the same explanations apply for the other components): $r_{new} = r_i$.

In one embodiment, pixel correction includes the modification of a pixel colour by a value equal to said value differential. For example, $g_{new} = g_i + \delta_1$ and $b_{new} = b_i + \delta_2$.

Figure 6B:
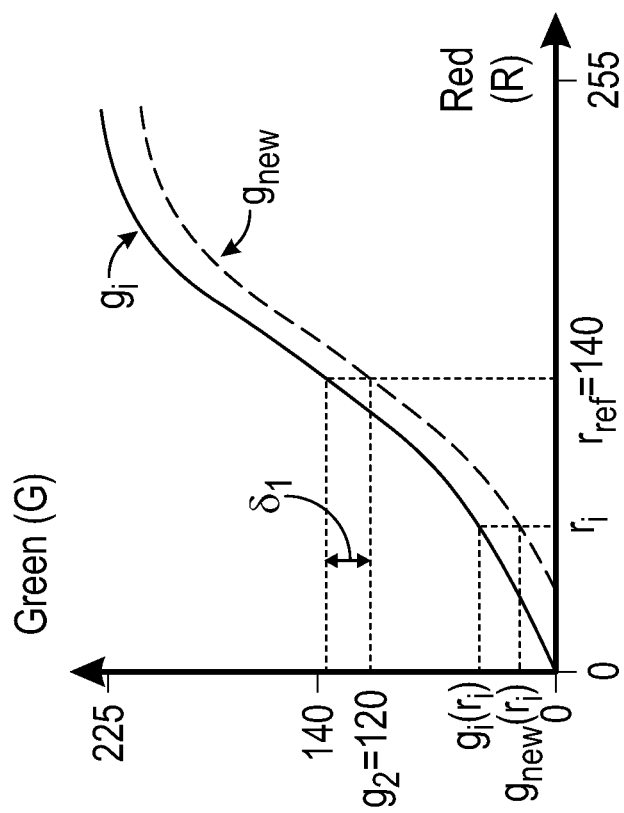
FIG. 6 illustrates different colour correction profiles of a pixel in the method of FIG. 5.
Figure 6A:
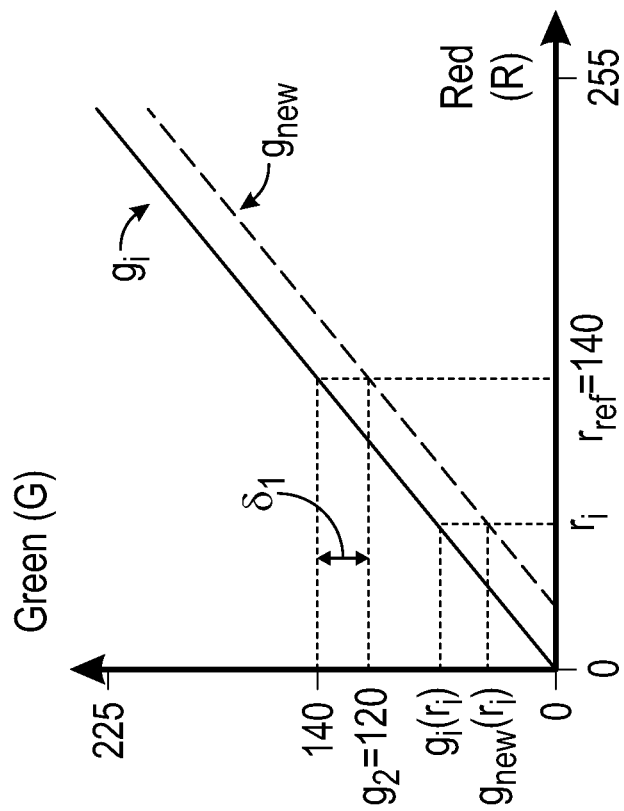
Figure 6D:
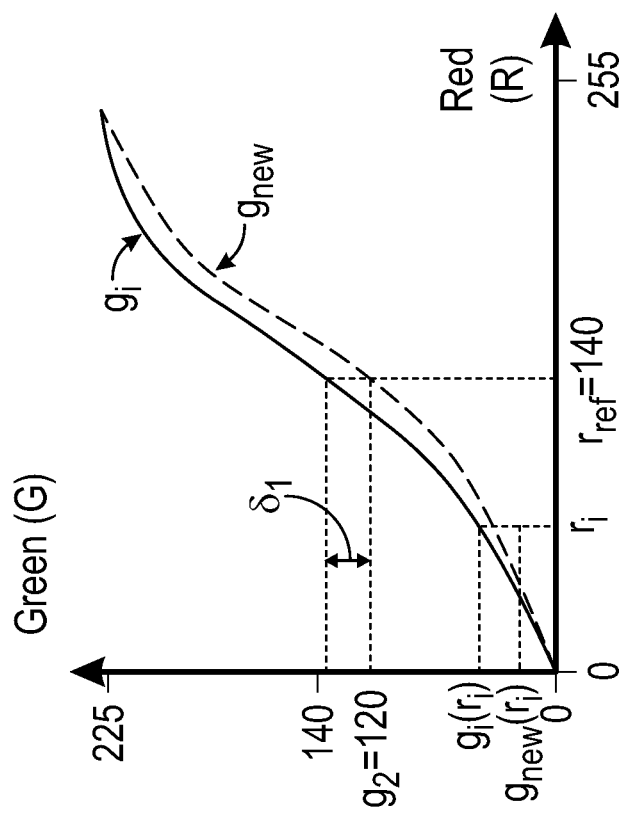

FIG. 6a illustrates this change for the green component g, in a screen configuration where the red-green iso-luminance is linear. FIG. 6b illustrates a similar modification in the case where the red-green iso-luminance is random.

In another embodiment, pixel correction involves changing a pixel colour by a value that is a function of both the value differential and the distance of another pixel colour from the reference value. In this case, the idea is to introduce a correction that may vary depending on whether one is more or less far from the reference value from which the correction differentials $\delta_1$ and $\delta_2$ were determined. It allows in particular by defining the extreme values (0,0,0) and (255,255,255) as invariant by this correction, to keep the corrected values $r_{new}, g_{new}, b_{new}$ in the colorimetric space (therefore between 0 and 255 each).

Red is kept as the reference value. The other green and blue components are corrected by $\delta_1$ and $\delta_2$ respectively when the red component is 140, and corrected by a smaller value (depending on the distance from the red component to 140) when the pixel to be displayed has a red component different from 140. The correction is nil at values 0 and 255. Rounding is used because the colour components are necessarily integers.

Preferably, the function modifying $\delta_1$ and $\delta_2$ according to the distance of the red component at 140 (thus the distance between $r_{ref}$ and $r_i$) is preferably linear with respect to this distance.

Figure 6C:
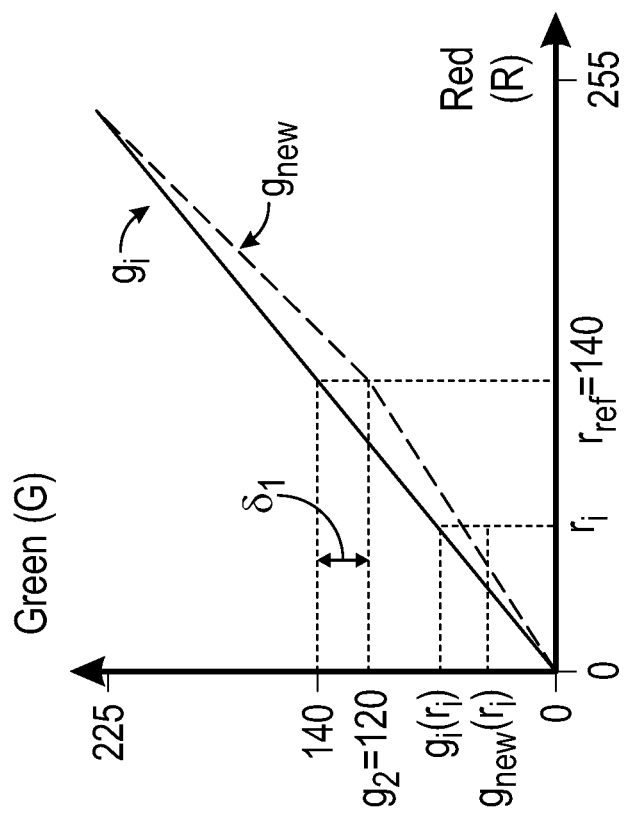

This configuration is illustrated by FIGS. 6c (linear red-green iso-luminance) and 6d (non-linear red-green iso-luminance). This function is therefore piecewise linear either side of the determined iso-luminance point, (140, 160) here for the Red-Green pair.

In this case, $g_{new}(r_i) = g_i(r_i) + \delta_1 * r_i / 140$ if $r_i < 140$
and $g_{new}(r_i) = g_i(r_i) + \delta_1 * (255 - r_i)/(255 - 140)$ if $r_i > 140$.

In other embodiments, the correction of the colour triplet ($r_i, g_i, i$) to be displayed is performed at constant pixel $P_i$ luminance.

Let's take the following example (other formulas exist for the skilled person) of a luminance calculated from the RGB triplet of colours:

$$L(r_i, g_i, b_i) = 0.2126 * r_i + 0.7152 * g_i + 0.0722 * b_i$$

These other embodiments consist in solving the three-unknown system formed by the following three equations:

$$i - (r_{new}, g_{new}, b_{new}) = L(r_i, g_i, b_i)$$

$$g_{new} = g_{new}(r_i)$$

$$b_{new} = b_{new}(r_i)$$

The method of calibrating a screen according to the invention makes it possible to display colours perceived in the same way (with respect to their iso-luminance) by different users using different screens.

Figure 7:
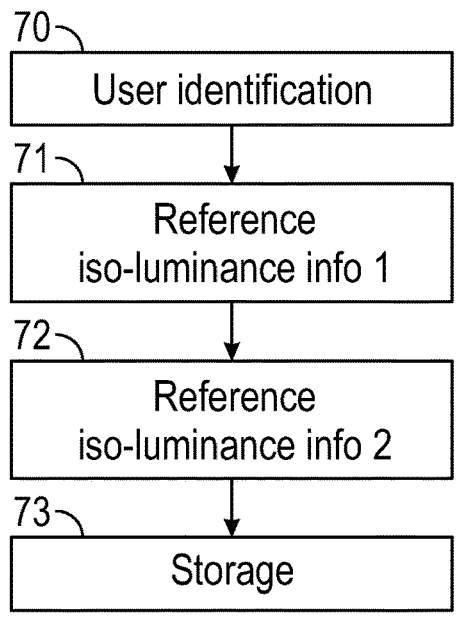
FIG. 7 illustrates, by means of a flowchart, a preliminary method for determining and recording identification/authentication information of an individual.
Figure 8:
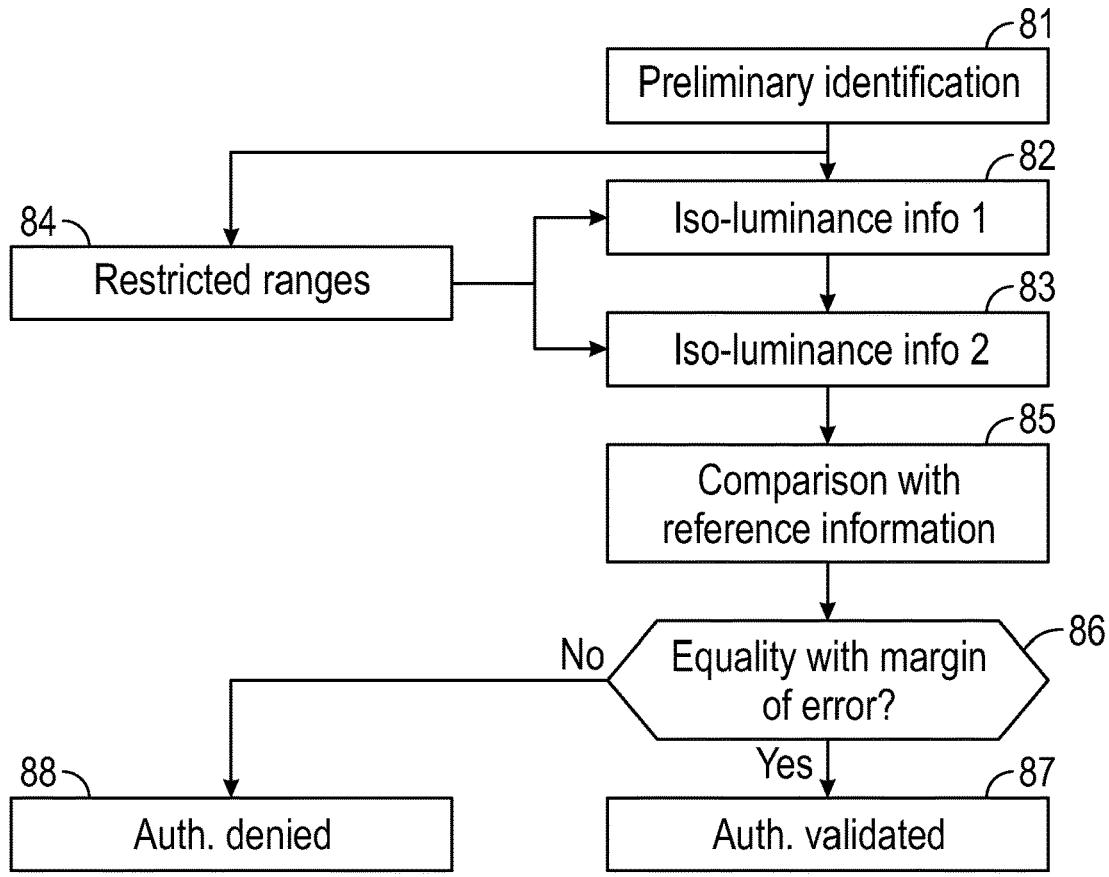
FIG. 8 illustrates, by means of a flowchart, a method for identifying or authenticating an individual based on iso-luminance information determined according to the method in FIG. 4, according to embodiments of the invention.

FIGS. 7 and 8 illustrate the application of the iso-luminance configuration for security purposes, for example, for identity verification (identity control) or access control (car, safe, building, door, database, on-line service such as a bank account) based on securing computer systems, including by identification and/or authentication.

The procedure for identifying or authenticating an individual can be implemented by system 1 in FIG. 1.

FIG. 7 illustrates preliminary steps for storing in system 30 identification/authentication information of individual 2, for example a user of the computer system, for the purpose of allowing subsequent identification or authentication, according to the teachings of the invention.

In step 70, a profile of user 2 is obtained that includes a unique user ID. For example, the user identifies himself to system 30 by PIN code, chip card, login/password, biometric identification, or any other means.

In step 71, a first iso-luminance information is determined for one of the user's eyes, using for example the procedure in FIG. 4. Typically, a colour pair among the red-green, red-blue and green-blue pairs of the red-green-blue colour space is considered. Step 71 provides a value determined for a first colour (e.g. green) when the second colour (e.g. red) takes a reference value (e.g. 140,0,0). The determined value is for example $g_2 = 120$ as in the above example in FIG. 5, and thus constitutes the first iso-luminance information determined.

In the optional step 72, a second iso-luminance information can be obtained for the same eye, also using the procedure in FIG. 4 for example. This second information can be obtained for another colour pair, for example red-blue in the example given above for which the value Blue=(0,0, 170) is obtained for the reference red $r_{ref}$=140 for Red (140,0,0).

Thus, two chromatic iso-luminance information, for example $g_2$=120 and $b_2$=170, are obtained for two different colour pairs among the red-green, red-blue and green-blue couples of the red-green-blue colour space. Each chromatic iso-luminance information includes a determined value, $g_{2a=120}$ and $b_2$=170, for a first colour (green and blue respectively) when the second colour (red in both cases) takes a reference value (140,0,0).

At step 73, the two chromatic iso-luminance information, in this case $g_2$=120 and $b_2$=170, for the eye considered are stored in memory of the computer system 30 in association with one user ID (here in the user profile).

These two pieces of information are reference chromatic iso-luminance information, noted $g_{ref}$ and $b_{ref}$, in the sense that they will be used in the process of FIG. 8 to validate or not a subsequent identification or authentication of the user 2. They are preferably stored in encrypted form, and/or in a protected memory (e.g. a secure module).

The preliminary process in FIG. 7 is now complete.

As shown in FIG. 8, user 2 now wants to access a service/system managed by system 30 that requires identification or authentication.

In step 81, user 2 performs a preliminary identification step. This step aims in particular to retrieve the user profile and the chromatic iso-luminance information of reference $g_{ref}$ and $b_{ref}$ associated with the user, before following the identification/authentication procedure (steps 82 and following).

Similar to step 70 above, this preliminary identification step may be based on a PIN code provided by the user, a user-specific chip card, a user login/password, a biometric identification of the user (morphometry, fingerprint, iris image), or any other means.

The process continues with steps 82 and 83 to determine the chromatic iso-luminance information $g_2$ and $b_2$ of the user's relevant eye for the same reference red colour (140, 0,0) as used in FIG. 7. These steps are similar to steps 50 and 51 or 71 and 72 described above. They therefore use the process in FIG. 4 for example.

In one embodiment intended to reduce the processing of these steps, a step 84 is provided for determining, depending on the identification of the user obtained in step 80, at least one restricted range (with respect to a range of possible values) of modification values to change over time the colour of the multicoloured pattern, typically bicoloured, to be modified when determining 82 and/or 83. Typically, the modification profile 410 to be used during these steps 82 and 83 can be only a part of the one shown in FIG. 3, for example only between 80 and 160 (if it is known that the identified user has a reference iso-luminance value of about 120). This restricted range can be indicated (via an identifier) in the user profile, or generated on the fly at random (around the user's reference iso-luminance value).

The process continues in step 85 by comparing the chromatic iso-luminance information determined in step(s) 82 and/or 83 with the corresponding reference chromatic iso-luminance information, as stored in step 73 for the user.

The comparison is not necessarily strict and may include a margin of error, such as a few units on the 0-255 scale of possible values for each colour component (step 86).

The identification or authentication of user 2 is only validated (step 87) if the iso-luminance information matches, i.e. if $g_2$ and $b_2$ determined in steps 82 and 83 are $g_{ref}$ and $b_{ref}$ respectively, for the eye in question. In this case, access to the service or system is authorized.

Otherwise, identification or authentication is refused (step 88).

Given the discrete and low number of possible iso-luminance configurations compared to the number of humans, identification or authentication based on iso-luminance information according to the invention is preferably combined with strong user identification/authentication (in step 80 above for example), for example from biometric data. Thus, identification or authentication based on iso-luminance information according to the invention secures biometric identification/authentication in that it guarantees that the user is actually alive.

The above example of identification/authentication is based on the configuration of iso-luminance perceived by one eye of the individual. However, it has been found that an individual's two eyes generally do not perceive colours in the same way, the difference in perception being slight or significant. It may therefore be possible, in a particular embodiment, to identify/authenticate the individual based on the iso-luminance configurations (described above) of both eyes. For example, a first validation step can be performed with the first eye (e.g. right eye), then a second validation step with the other eye. The safety of this embodiment is thus enhanced.

Alternatively, the difference in response between the individual's two pupils can be taken into account and used as an element of identification/authentication of the individual for the above-mentioned security purposes. For example, the difference between the two iso-luminance configurations (for example, the difference in green values when red is set to a reference value).

The foregoing examples are only embodiments of the invention that are not limited to them.

The invention claimed is:

1. A method for controlling a computer process in a personalised manner in a computer system, comprising the following steps:
   determining at least one chromatic iso-luminance information for an individual, wherein determining the at least one chromatic iso-luminance information comprises:
   submitting the individual to a dynamic multicolour stimulus comprising displaying, on a display device of the computer system, a multicolour pattern, at least two colours of which are periodically inverted at a so-called marking frequency,
   controlling a change over time of at least one of the at least two colours of the multicolour pattern when displaying the dynamic multicolour stimulus, to vary a displayed luminance of that colour and to vary a luminance difference between the at least two colours,
   acquiring, by an image acquisition device, an oscillatory response of at least one pupil of the individual, when displaying the dynamic multicolour stimulus,
   generating, from the acquired oscillatory response, a signal representative of a power of the oscillatory response of the at least one pupil as a function of the change over time of at least one of the at least two colours and a difference in luminance between the at least two colours when displaying the dynamic multi-colour stimulus, and
   wherein the at least one chromatic iso-luminance information comprises a bicolour iso-luminance configuration of the at least two colours in the dynamic multicolour stimulus corresponding to a minimum of the signal representative of the power, and using the at least one chromatic iso-luminance information to determine input data of the computer process in the computer system.

2. The method according to claim 1, wherein the computer process is a process for a calibration of a display screen of the computer system, in which a display of a pixel is corrected as a function of said at least one chromatic iso-luminance information.

3. The method according to claim 2, wherein the at least one chromatic iso-luminance information comprises, for at least one colour pair among a red-green pair, a red-blue pair, and a green-blue pair of a red-green-blue colour space, a value determined for a first colour when a second colour takes a reference value.

4. The method according to claim 3, in which a default chromatic iso-luminance value of the first colour is obtained for an initial calibration of the display screen when the second colour takes a reference value, and the correcting the pixel comprises adjusting a first colour or a second colour of the pixel according to a value differential between the default chromatic iso-luminance value and the determined value of the chromatic iso-luminance.

5. The method according to claim 4, wherein the correction of the pixel comprises modifying the first colour or the second colour of the pixel by a value equal to said value differential.

6. The method according to claim 4, wherein the correction of the pixel comprises modifying the first colour of the pixel by a value that is a function of both the value differential and a distance of the second colour of the pixel from the reference value.

7. The method according to claim 6, wherein this function is linear with respect to said distance between the second colour of the pixel and the reference value.

8. The method according to claim 3, comprising determining two chromatic iso-luminance information for two different colour pairs among the red-green pair, the red-blue pair and the green-blue pair of the red-green-blue colour space, each chromatic iso-luminance information comprising a determined value for a first colour when the second colour takes a reference value.

9. The method according to claim 2, comprising determining two chromatic iso-luminance information for two different colour pairs among a red-green pair, a red-blue pair, and a green-blue pair of the red-green-blue colour space, each chromatic iso-luminance information comprising a determined value for a first colour when a second colour takes a reference value.

10. The method according to claim 9, wherein the correction of a pixel on the display screen comprises adjusting a colour triplet defining the pixel according to an initial calibration of the display screen, based on two value differentials obtained for the two colour pairs, each value differential representing the difference between a default value of chromatic iso- luminance for the first colour of the colour pair when the second colour takes the reference value and the determined value of chromatic iso-luminance.

11. The method according to claim 10, wherein the colour triplet is adjusted at constant pixel luminance.

12. The method according to claim 10, wherein the adjustment of the colour triplet is performed at constant value of one of its colour components.

13. The method according to claim 1, wherein the computer process using the at least one chromatic iso-luminance information is a procedure for identifying or authenticating the individual.

14. The method according to claim 13, further comprising comparing the at least one determined chromatic iso-luminance information with at least one reference chromatic iso-luminance information stored in a memory of the computer system in association with an identifier of individual, and validating an identification or authentication of the individual only if the chromatic iso-luminance information matches.

15. The method according to claim 14, comprising determining two pieces of chromatic iso-luminance information for two different colour pairs among a red-green pair, a red-blue pair and a green-blue pair of the red-green-blue colour space, each chromatic iso-luminance information comprising a determined value for a first colour when the second colour takes a reference value.

16. The method according to claim 15, further comprising a preliminary step of identifying individual to retrieve the at least one reference chromatic iso-luminance information associated with said individual, prior to said comparison.

17. The method according to claim 14, further comprising a preliminary step of identifying individual to retrieve the at least one reference chromatic iso-luminance information associated with said individual, prior to said comparison.

18. The method according to claim 14, further comprising determining, based on the identification of the individual, at least a limited range of change values for changing over time the colour to be changed of the multicolour pattern when determining chromatic iso-luminance information.

19. The method according to claim 13, further comprising determining, based on an identification of the individual, at least a limited range of change values for changing over time the colour to be changed of the multicolour pattern when determining chromatic iso-luminance information.

20. A system for controlling a computer process in a personalised manner in a computer system, comprising:
a subsystem for determining at least one chromatic iso-luminance information for an individual, and
a process control module configured to use the at least one chromatic iso-luminance information to determine input data of the computer process in the computer system,
the subsystem for determining iso-luminance information comprising:
a display device,
a computer module for stimulating the individual by means of a dynamic multicolour stimulus, the computer module controlling a display, on the display device, of a multicolour pattern, at least two colours of which are periodically inverted at a so-called marking frequency,
a colour controller configured to change over time at least one of the at least two colours of the multicolour pattern when displaying the dynamic multicolour stimulus, to vary a displayed luminance of that colour and to vary a luminance difference between the at least two colours,
an image acquisition device for acquiring an oscillatory response of at least one pupil of the individual, when displaying the dynamic multicolour stimulus,
an indicator or biomarker generator configured to generate, from the acquired oscillatory response, a signal representative of a power of the oscillatory response of the at least one pupil as a function of a change over time of at least one of the at least two colours and a difference in luminance between the at least two colours when displaying the dynamic multicolour stimulus, and an iso-luminance determination unit configured to determine the at least one chromatic iso- luminance information, wherein said at least one chromatic iso-luminance information comprises a bicolour iso-luminance configuration of the at least two colours in the dynamic multicolour stimulus corresponding to a minimum of the signal representative of the power.

* * * * *